(12) United States Patent
Carrara et al.

(10) Patent No.: US 7,387,788 B1
(45) Date of Patent: *Jun. 17, 2008

(54) PHARMACEUTICAL COMPOSITIONS OF NICOTINE AND METHODS OF USE THEREOF

(75) Inventors: R. Dario Norberto Carrara, Oberwil (CH); Arnaud Grenier, Steinbrunn le Haut (FR); Celine Besse, Saint Louis (FR)

(73) Assignee: Antares Pharma IPL AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/492,568

(22) Filed: Jul. 24, 2006

Related U.S. Application Data

(63) Continuation-in-part of application No. 11/371,042, filed on Mar. 7, 2006, which is a continuation of application No. PCT/EP2004/011175, filed on Oct. 6, 2004.

(60) Provisional application No. 60/510,613, filed on Oct. 10, 2003.

(51) Int. Cl.
  *A61K 13/00* (2006.01)
  *A61K 31/465* (2006.01)
(52) U.S. Cl. .................................. 424/449; 514/343
(58) Field of Classification Search ................. 424/449, 424/751; 514/343
  See application file for complete search history.

(56) References Cited

U.S. PATENT DOCUMENTS

| | | | |
|---|---|---|---|
| 4,597,961 A | 7/1986 | Etscorn | 424/28 |
| 4,704,406 A | 11/1987 | Stanislaus et al. | 514/570 |
| 4,832,953 A | 5/1989 | Campbell et al. | 424/448 |
| 5,230,896 A | 7/1993 | Yeh et al. | 424/443 |

(Continued)

FOREIGN PATENT DOCUMENTS

EP  1325 752 A2  6/2003

(Continued)

OTHER PUBLICATIONS

Ralph Lipp et al., XP-002121357, "Selection And Use Of Crystallization Inhibitors For Matrix-Type Transdermal Drug-Delivery Systems Containing Sex Steroids", Journal of Pharm. Pharmacol, vol. 50, pp. 1343-1349 (1998).

(Continued)

*Primary Examiner*—Johann Richter
*Assistant Examiner*—Konata M. George
(74) *Attorney, Agent, or Firm*—Winston & Strawn LLP

(57) ABSTRACT

The present invention comprises non occlusive compositions for transdermal delivery of nicotine, and more particularly pharmaceutically acceptable salts thereof, and methods of making same. The composition may, for example, be a gel suitable for transdermal or transmucosal applications. The compositions of the present invention typically comprise a mixture of water and alcohol, and a solvent system having a mono alkyl ether of diethylene glycol and a glycol present in specified ratios and in specific amounts, wherein the pH of the gel is usually between a pH of 5.5 and 7. The compositions may include further components, for example, the hydroalcoholic vehicle may further comprise additional penetration enhancer(s), buffering agent(s), antioxidant(s), stabilizer(s) and/or gelling agent(s). The invention also relates to a method for the sustained delivery of nicotine pharmaceutically acceptable salts to treat a variety of conditions and disorders.

33 Claims, 9 Drawing Sheets

U.S. PATENT DOCUMENTS

| | | | | |
|---|---|---|---|---|
| 5,278,176 | A | 1/1994 | Lin | 514/343 |
| 5,580,574 | A | 12/1996 | Behl et al. | 424/449 |
| 5,603,947 | A | 2/1997 | Wong et al. | 424/448 |
| 5,633,008 | A | 5/1997 | Osborne et al. | 424/448 |
| 5,658,587 | A | 8/1997 | Santus et al. | 424/448 |
| 5,662,890 | A | 9/1997 | Punto et al. | 424/59 |
| 5,783,207 | A | 7/1998 | Stanley et al. | 424/440 |
| 5,891,462 | A | 4/1999 | Carrara | 424/449 |
| 5,932,243 | A | 8/1999 | Fricker et al. | 424/450 |
| 5,935,604 | A | 8/1999 | Illum | 424/501 |
| 6,034,079 | A | 3/2000 | Sanberg et al. | 514/225.8 |
| 6,165,497 | A | 12/2000 | Osborne et al. | 424/448 |
| 6,166,044 | A | 12/2000 | Samdborn et al. | 514/343 |
| 6,267,985 | B1 | 7/2001 | Chen et al. | 424/451 |
| 6,299,900 | B1 | 10/2001 | Reed et al. | 424/449 |
| 6,383,471 | B1 | 5/2002 | Chen et al. | 424/45 |
| 6,417,205 | B1 | 7/2002 | Cooke et al. | 514/343 |
| 6,426,078 | B1 | 7/2002 | Bauer et al. | 424/401 |
| 6,465,005 | B1 | 10/2002 | Biali et al. | 424/449 |
| 6,479,076 | B2 | 11/2002 | Blank | 424/484 |
| 6,596,740 | B2 | 7/2003 | Jones | 514/343 |
| 6,828,336 | B2 | 12/2004 | Walling | 514/343 |
| 6,911,475 | B1 | 6/2005 | Cesaro et al. | 514/567 |
| 6,995,265 | B2 | 2/2006 | Comins et al. | 546/14 |
| 7,029,692 | B1 | 4/2006 | Bracht | 424/449 |
| 2004/0213744 | A1* | 10/2004 | Lulla et al. | 424/45 |
| 2004/0219197 | A1 | 11/2004 | Carrara et al. | 424/449 |
| 2006/0153905 | A1* | 7/2006 | Carrara et al. | 424/449 |

FOREIGN PATENT DOCUMENTS

| | | |
|---|---|---|
| WO | WO 95/18603 | 7/1995 |
| WO | WO 95/29678 | 11/1995 |

OTHER PUBLICATIONS

Pramila N. Kotiyana et al., "Eudragits: Role As Crystallization Inhibitors In Drug-In-Adhesive Transdermal Systems Of Estradiol", European Journal of Pharmaceutics and Biopharmaceutics, vol. 52 pp. 173-180 (2001).

Katrin Moser et al., "Passive Skin Penetration Enhancement And Its Quantification In Vitro", European Journal of Pharmaceutics and Biopharmaceutics, vol. 52 pp. 103-112 (2001).

P. Mura et al., XP-002315954, "Evaluation Of Transcutol As A Clonazepam Transdermal Permeation Enhancer From Hydrophilic Gel Formulations", European Journal of Pharmaceutical Sciences, vol. 9, pp. 365-372 (2000).

* cited by examiner

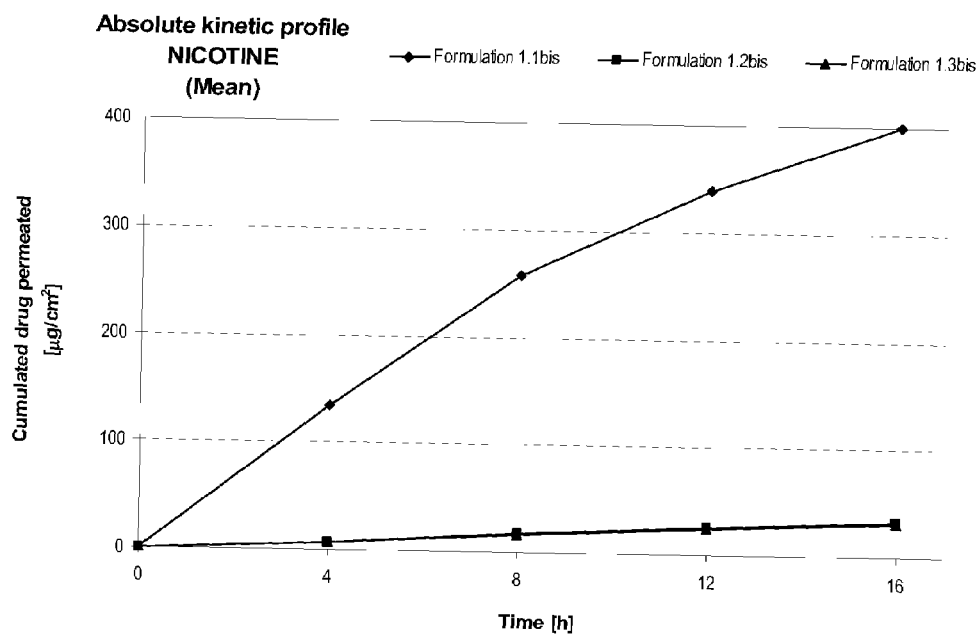
FIGURE 1Abis
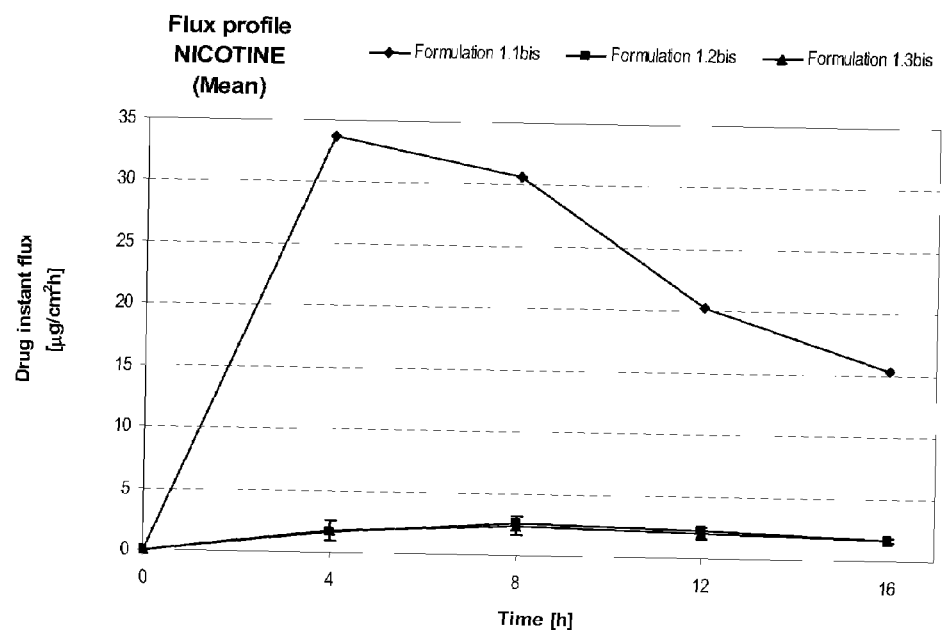
FIGURE 2Abis

PHARMACEUTICAL COMPOSITIONS OF NICOTINE AND METHODS OF USE THEREOF

CROSS REFERENCE TO RELATED APPLICATIONS

This application is a continuation-in-part of co-pending application Ser. No. 11/371,042, filed Mar. 7, 2006, which is a continuation of International application PCT/EP2004/011175 filed Oct. 6, 2004 and claims the benefit of U.S. Provisional Application No. 60/510,613, filed Oct. 10, 2003. The content of each prior application is expressly incorporated herein by reference.

TECHNICAL FIELD

The present invention relates to novel transdermal or transmucosal pharmaceutical formulations, including compositions and dosage forms, of nicotine and its pharmaceutically acceptable salts thereof, and a hydroalcoholic solvent system, wherein the solvent system includes monoalkyl glycol ethers and glycols in specific ratios.

Described herein are formulations that are useful and efficacious for transdermal delivery, as well as methods of use and methods of manufacturing for such formulations.

BACKGROUND OF THE INVENTION

Transdermal delivery, i.e. the ability to deliver pharmaceuticals agents into and through skin surfaces, provides many advantages over oral or parenteral delivery techniques. In particular, transdermal delivery provides a safe, convenient and non invasive alternative to traditional administration systems that can provide a straightforward dosage regimen, relatively slow release of the drug into a patient's system, and control over blood concentrations of the drug. In contrast to oral administration, transdermal delivery typically does not produce the plasmatic peaks and valleys created by oral delivery and G.I. tract absorption. Second, transdermal delivery causes no gastrointestinal irritation, does not present restrictions around the time that the drug should be administered or whether or not the patient may eat afterwards. In particular, once-a-day transdermal delivery offers ease of use and is convenient, without the requirement to remember to take a drug at a specific time. Third, transdermal delivery improves patient compliance for patients who cannot swallow medication, for drugs with unpleasant taste and/or undergoing significant metabolism in the liver; the resulting increased bioavailability, which means that smaller doses may be used for the same drug, is responsible for minimized side effects. In contrast to parenteral administration, transdermal delivery typically does not cause pain and/or anxiety associated with needles, and does not present the risk of introducing infection to treated individuals, the risk of contamination or infection of health care workers caused by accidental needle-sticks and the risk of disposal of used needles.

The advantage of transdermal delivery is particularly enhanced in case of hydrophilic drugs, because of the molecular nature of the G.I. tract. As a lipid membrane, the G.I. tract possesses hydrophobic properties, thus the more hydrophilic a drug is, and the more likely it is to be absorbed poorly through the G.I. tract. A well known example of this problem is sodium alendronate, a bisphosphonate, which needs to be administered in very large doses because only a very small fraction of the drug (about 0.6) % is absorbed indeed when administered orally (please refer to FOSA-MAX® Tablets and Oral Solutions Prescribing Information, issued by Merck & Co., Inc., the entire content is incorporated herein for information).

However, despite its clear advantages, transdermal delivery also poses inherent challenges, in part because of the nature of skin. Skin is essentially a thick membrane that protects the body by acting as a barrier. Consequently, passive delivery through intact skin necessarily entails the transport of molecules through a number of structurally different tissues, including the stratum corneum, the viable epidermis, the papillary dermis and the capillary walls in order for the drug to gain entry into the blood or lymph system. Each tissue features a different resistance to penetration, but the stratum corneum is the strongest barrier to the absorption of transdermal and topical drugs. The tightly packed cells of the stratum corneum are filled with keratin. The keratinization and density of the cells may be responsible for skin's impermeability to certain drugs. Transdermal delivery systems must therefore be able to overcome the various resistances presented by each type of tissue.

In recent years, advances in transdermal delivery include the formulation of skin penetration enhancing agents, also known as permeation enhancers. Permeation enhancers are often lipophilic chemicals that readily move into the stratum corneum and enhance the movement of drugs through the skin. Energy-assisted skin permeation techniques also have emerged to improve transdermal delivery, including heat, ultrasound, iontophoresis, and electroporation. But even with these methodologies, only a limited number of drugs can be administered transdermally without problems such as sensitization or irritation occurring.

Transdermal delivery is different from topical delivery. Drugs administered transdermally are absorbed through skin or mucous membranes and provide effects beyond the application site. In contrast, purpose of a topical drug, e.g., antibiotic ointment, anti-acne cream, hair-growing lotion, anti-itching spray, is to administer medication at the site of intended action. Topical medications typically should be designed not to permit significant drug passage into the patient's blood and/or tissues. Topical formulations are often used to treat infections or inflammations. They also are used as cleansing agents, astringents, absorbents, keratolytics, and emollients. The vehicle of a topical treatment, i.e. the non-active component(s) that carries the active ingredient(s), may interact with the active ingredient(s), changing the drug's effectiveness. The vehicle may also cause skin irritation or allergic reactions in some patients. Thus, the vehicle must be selected with extreme care. Topical formulations may be prepared as pastes, gels, creams, ointments, lotions, solutions, or aerosols. Occlusion with household plastic wrap, bandages, plasters, or plastic tape, is often used in conjunction with topical treatments to improve the drug's absorption and its effectiveness. Typically non-occlusive dosage forms are applied to the skin or mucosa and are left uncovered and open in the atmosphere. Because the non-occlusive dosage form is left uncovered, unwanted transfer of the pharmaceutical formulation to the clothing of the user or even to other individuals in close proximity to the user is unavoidable. Other drawbacks of the non-occlusive dosage form include evaporation of the formulation, removal of the formulation from the skin or mucosa, for example, by bathing or by other activities, and the non absorption of the formulation through the skin, which is discussed below.

The inefficiencies of drug permeation across or through the skin or mucosa barriers are known. It is also known that the permeation of a drug in a non-occlusive transdermal or transmucosal dosage form can be as little as 1% and usually is no more than 15%. Thus, a vast majority of the active drug remains unabsorbed on the skin or mucosa surface. Because the vast majority of the drug remains on the skin and does not penetrate the skin or mucosa surfaces, the bioavailability of the particular drug is not optimal, and also a high risk of contamination of other individuals in close proximity to the user is presented by the unwanted transfer of the pharmaceutical formulation in the non-occlusive dosage form.

Problems associated with the unwanted transfer of a particular pharmaceutical formulation to others are well documented. For example, Delanoe et al. reported the androgenization of female partners of volunteers applying a testosterone gel preparation during contraceptive studies (Delanoe, D., Fougeyrollas, B., Meyer, L. & Thonneau, P. (1984): "Androgenisation of female partners of men on medroxyprogesterone acetate/percutaneous testosterone contraception", Lancet 1, 276-277). Similarly, Yu et al. reported virilization of a two-year-old boy after incidental and unintentional dermal exposure to a testosterone cream applied to his father's arm and back (Yu,Y. M., Punyasavatsu, N., Elder, D. & D'Ercole, A. J. (1999): "Sexual development in a two-year old boy induced by topical exposure to testosterone", Pediatrics, 104, 23).

Moreover, the patient information brochure for ANDRO-GEL® (1% testosterone gel from Unimed Pharmaceuticals Inc.) emphasizes the potential for transfer of testosterone to other people and/or clothing and the brochure includes safety measures to be taken by the individual using the non-occlusive dosage form.

One way to overcome or minimize this contamination issue is to physically protect the transdermal dosage form by covering skin with the applied pharmaceutical formulation means of a patch device, a fixed reservoir, an application chamber, a tape, a bandage, a sticking plaster, or the like, which remain on the skin at the site of application of the formulation for a prolonged length of time. This is usually accomplished with occlusive dosage forms.

Occlusive dosage forms present some advantages over non-occlusive dosage forms such as assisting the rate of penetration of drugs across the skin by maintaining the thermodynamic activity of the drug close to its maximum (the thermodynamic activity of a drug in a dermal formulation is proportional to the concentration of the drug and the selection of the vehicle, and according to the laws of thermodynamics, the maximum activity of a drug is related to that of the pure drug crystal). However occlusive dosage forms also exhibit several major drawbacks. For example, occlusive dosage forms present a high potential of local skin irritation caused by the prolonged contact on the skin of the drug, volatiles, vehicle excipients, and the adhesive used to attach the occlusive device, e.g., the patch, to the skin. In addition, the occlusive nature of certain occlusive dosage forms, such as the patch device, also restrict the natural ability of the skin to "breathe," and thereby increases the risk of irritation.

In addition to the aforementioned drawbacks of occlusive dosage forms, significant serious hazards have been documented regarding the high drug loading that is specific to patches. For example, several cases of abuses with remaining fentanyl in fentanyl patches have been reported. See, Marquardt K. A., Tharratt R. S., "Inhalation abuse of fentanyl patch", J Toxicol Clin. Toxicol. 1994; 32(1):75-8; Marquardt K. A., Tharratt R. S., Musallam N. A., "Fentanyl remaining in a transdermal system following three days of continuous use.", Ann Pharmacother. 1995 October; 29(10):969-71; Flannagan L M, Butts J D, Anderson W H., "Fentanyl patches left on dead bodies—potential source of drug for abusers.", J Forensic Sci. 1996 March; 41(2):320-1. Severe incidental intoxication cases have also been documented. See Hardwick Jr., W, King, W., Palmisano, P., "Respiratory Depression in a Child Unintentionally Exposed to Transdermal Fentanyl Patch", Southern Medical Journal, September 1997.

Patch products typically contain patient information, which clearly indicate the risks discussed above. For instance, OXYTROL™ (an oxybutynin patch commercialized by WATSON Pharmaceuticals, Inc. USA) contains patient information that indicates the following warning: "Since the patch will still contain some oxybutynin, throw it away so that it can not be accidentally worn or swallowed by another person, especially a child." The high level of active drug residues is thus a critical drawback of patches. Such accidents could not occur with the use of gel formulations.

Although attempts have been made to overcome drawbacks associated with both occlusive and non-occlusive drug forms, such attempts have been futile. For example, as noted above, one drawback of non-occlusive dosage forms is evaporation of the formulation, which is left open in the atmosphere. The formulation of non-occlusive supersaturated systems could have achieved an ideal merge but transdermal formulations, which rely on supersaturation technologies, present a major drawback of formulation instability, both prior to and during application to the skin due to solvent evaporation. See Davis A F and Hadgraft J—Supersaturated solutions as topical drug delivery systems, Pharmaceutical Skin Penetration Enhancement, Marcel Dekker Inc, New York (1993) 243-267 ISBN 0 8247 9017 0, which is incorporated herein by reference.

Notably, extraordinary physicochemical changes occur with the evaporation of the solvent system, which result in modifications of the concentration of the active agent, which may even lead to drug precipitation, thereby altering the diffusional driving force of the formulation. See Ma et al, Proceed. Intern. Symp. Control. Rel. Bioact. Mater., 22 (1995). Consequently, the percutaneous absorption of the active agent may be quite different from that when the solvent was present.

In addition, controlling drug crystallization is of particular interest for non-occlusive transdermal systems. Campbell et al. resorted to a method of heating a crystalline hydrate to a temperature above the melting point in order to prevent the crystallization of the formulation. See, U.S. Pat. No. 4,832, 953. Ma et al found that PVP added to the matrix acts as an effective crystallization inhibitor for norethindrone acetate transdermal delivery systems. See, Int. J. of Pharm. 142 (1996) pp. 115-119). DE-A-4210711 affirms that cholesterol and $SiO_2$ are crystallization inhibitors for 17-.beta.-estradiol transdermal delivery system. WO 95/18603 describes soluble PVP as crystal inhibitor for patch devices and affirms that soluble PVP increases the solubility of a drug without negatively affecting the adhesion or the rate of drug delivery from the pressure-sensitive adhesive composition.

Additionally, the inhibition of crystallization in transdermal devices was reported by Biali et al. See, U.S. Pat. No. 6,465,005 in which it is described that the use of a steroid (estradiol for instance) as an additive in a process of manufacture or storage of a transdermal device acts as a crystallization inhibitor during storage of the device.

Further, transdermal delivery from semi-solid formulations faces opposite requirements. The drug delivery system should enable absorption of an extensive amount of active drug through the skin within the shortest period of time in order to prevent contamination of individuals, transfer to clothing or accidental removing. The drug delivery system should also provide sustained release of the active drug over 24 hours ideally, so that only once-daily application is required. This drug delivery system should also prevent drug crystallization at the application surface area.

Drug delivery systems having such properties may be achieved by combining various solvents. A volatile solvent may be defined as a solvent that changes readily from solid or liquid to a vapor, that evaporates readily at normal temperatures and pressures. Here below is presented data for some usual solvents, where volatility is reflected by the molar enthalpy of vaporization $\Delta_{vap}H$, defined as the enthalpy change in the conversion of one mole of liquid to gas at constant temperature. Values are given, when available, both at the normal boiling point $t_b$, referred to a pressure of 101.325 kPa (760 mmHg), and at 25° C. (From "Handbook of Chemistry and Physics, David R. Lide, 79$^{th}$ edition (1998-1999)—Enthalpy of vaporization (6-100 to 6-115). Stanislaus et al. (U.S. Pat. No. 4,704,406 on Oct. 9, 2001) defined as volatile solvent a solvent whose vapor pressure is above 35 mm Mg when the skin temperature is 32° C., and as non-volatile solvent a solvent whose vapor pressure is below 10 mm Mg at 32° C. skin temperature. Examples of non-volatile solvents include, but are not limited to, propylene glycol, glycerin, liquid polyethylene glycols, or polyoxyalkylene glycols. Examples of volatile solvents include, but are not limited to, ethanol, propanol, or isopropanol.

TABLE 1

Enthalpy of vaporization of certain solvents

|  | $t_b$ | $\Delta_{vap}H$ ($t_b$) | $\Delta_{vap}H$ (25° C.) |
|---|---|---|---|
| Ethanol | 78.3 | 38.6 | 42.3 |
| Propan-2-ol (isopropanol) | 82.3 | 39.9 | 45.4 |
| Propanol | 97.2 | 41.4 | 47.5 |
| Butan-2-ol | 99.5 | 40.8 | 49.7 |
| Butan-1-ol | 117.7 | 43.3 | 52.4 |
| Ethylene glycol mono methyl ether | 124.1 | 37.5 | 45.2 |
| Ethylene glycol mono ethyl ether | 135.0 | 39.2 | 48.2 |
| Ethylene glycol mono propyl ether | 149.8 | 41.4 | 52.1 |
| 1,2-Propylene glycol | 187.6 | 52.4 | Not available |
| Diethylene glycol mono methyl ether | 193.0 | 46.6 | Not available |
| Diethylene glycol mono ethyl ether | 196.0 | 47.5 | Not available |
| 1,3-Propylene glycol | 214.4 | 57.9 | Not available |
| Glycerin | 290.0 | 61.0 | Not available |

Numerous authors have investigated evaporation and transdermal penetration from solvent systems. For Example, Spencer et al. (Thomas S. Spencer, "Effect of volatile penetrants on in vitro skin permeability", AAPS workshop held in Washington D.C. on Oct. 31-Nov. 1, 1986) established that the relationship between volatility and penetration is not absolute and depends on many parameters such as for instance hydration of the tissue or the solubility of the penetrant in the tissue. Stinchcomb et al. reported that the initial uptake of a chemical (hydrocortisone, flurbiprofen) from a volatile solvent system (acetone) is more rapid than that from a non-volatile solvent system (aqueous solution). With an aqueous solution, close to the saturation solubility of the chemical, the driving force for uptake remains more or less constant throughout the exposure period. Conversely, for a volatile vehicle which begins evaporating from the moment of application, the surface concentration of the chemical increases with time up to the point at which the solvent has disappeared; one is now left with a solid film of the chemical from which continued uptake into the stratum corneum may be very slow and dissolution-limited.

Risk assessment following dermal exposure to volatile vehicles should pay particular attention, therefore, to the duration of contact between the evaporating solvent and the skin (Audra L. Stinchcomb, Fabrice Pirot, Gilles D. Touraille, Annette L. Bunge, and Richard H. Guy, "Chemical uptake into human stratum corneum in vivo from volatile and non-volatile solvents", Pharmaceutical Research, Vol. 16, No 8, 1999). Kondo et al. studied bioavailability of percutaneous nifedipine in rats from binary (acetone and propylene glycol PG or isopropyl myristate IPM) or ternary (acetone-PG-IPM) solvent systems, compared with the results from simple PG or IPM solvent systems saturated with the drug. (Kondo et al. S, Yamanaka C, Sugimoto I., "Enhancement of transdermal delivery by superfluous thermodynamic potential. III. Percutaneous absorption of nifedipine in rats", J Pharmaco Biodyn. 1987 December; 10(12):743-9).

U.S. Pat. No. 6,299,900 to Reed et al. discloses a non-occlusive, percutaneous, or transdermal drug delivery system—having active agent, safe and approved sunscreen as penetration enhancer, and optional volatile liquid. The invention describes a transdermal drug delivery system, which comprises at least one physiologically active agent or prodrug thereof and at least one penetration enhancer of low toxicity being a safe skin-tolerant ester sunscreen. The composition comprises an effective amount of at least one physiologically active agent, at least one non-volatile dermal penetration enhancer; and at least one volatile liquid.

U.S. Pat. No. 5,891,462 to Carrara discloses a pharmaceutical formulation in the form of a gel suitable for the transdermal administration of an active agent of the class of estrogens or of progestin class or of a mixture thereof, comprising lauryl alcohol, diethylene glycol mono ethyl ether and propylene glycol as permeation enhancers.

Mura et al. describe the combination of diethylene glycol mono ethyl ether and propylene glycol as a transdermal permeation enhancer composition for clonazepam (Mura P., Faucci M. T., Bramanti G., Corti P., "Evaluation of transcutol as a clonazepam transdermal permeation enhancer from hydrophilic gel formulations", Eur. J. Pharm. Sci., 2000 February; 9(4): 365-72)

Williams et al. reports the effects of diethylene glycol mono ethyl ether (TRANSCUTOL™) in binary co-solvent systems with water on the permeation of a model lipophilic drug across human epidermal and silastic membranes (A. C. Williams, N. A. Megrab and B. W. Barry, "Permeation of oestradiol through human epidermal and silastic membranes from saturated TRANSCUTOL®/water systems", in Prediction of Percutaneous Penetration, Vol. 4B, 1996). Many references may also illustrate the effect of TRANSCUTOL™ as an intracutaneous drug depot builder well known to one skilled in the art.

U.S. Pat. No. 5,658,587 to Santus et al. discloses transdermal therapeutic systems for the delivery of alpha adrenoceptor blocking agents using a solvent enhancer system comprising diethylene glycol mono ethyl ether and propylene glycol.

U.S. Pat. No. 5,662,890 to Punto et al. discloses alcohol-free cosmetic compositions for artificially tanning the skin containing a combination of diethylene glycol monoethyl ether and dimethyl isosorbide as permeation enhancer.

U.S. Pat. No. 5,932,243 to Fricker et al. discloses a pharmaceutical emulsion or microemulsion preconcentrate for oral administration of macrolide containing a hydrophilic carrier medium consisting of diethylene glycol mono ethyl ether, glycofurol, 1,2-propylene glycol, or mixtures thereof.

U.S. Pat. Nos. 6,267,985 and 6,383,471 to Chen et al. disclose pharmaceutical compositions and methods for improved solubilization of triglycerides and improved delivery of therapeutic agents containing diethylene glycol mono ethyl ether and propylene glycol as solubilizers of ionizable hydrophobic therapeutic agents.

U.S. Pat. No. 6,426,078 to Bauer et al. discloses an oil-in water microemulsion containing diethylene glycol mono ethyl ether or propylene glycol as co-emulsifier of lipophilic vitamins.

Many research experiments have been carried out on diethylene glycol mono ethyl ether (marketed under the trademark TRANSCUTOL™ by Gattefosse) as an intracutaneous drug depot builder. For example, Ritschel, W. A., Panchagnula, R., Stemmer, K., Ashraf, M., "Development of an intracutaneous depot for drugs. Binding, drug accumulation and retention studies, and mechanism depot for drugs", Skin Pharmacol, 1991; 4: 235-245; Panchagnula, R. and Ritschel, W. A., "Development and evaluation of an intracutaneous depot formulation of corticosteroids using TRANSCUTOL® as a cosolvent, in vitro, ex vivo and in-vivo rat studies", J. Pharm. Pharmacology. 1991; 43: 609-614; Yazdanian, M. and Chen, E., "The effect of diethylene glycol mono ethyl ether as a vehicle for topical delivery of ivermectin", Veternary Research Com. 1995; 19: 309-319; Pavliv, L., Freebern, K., Wilke, T., Chiang, C-C., Shetty, B., Tyle, P., "Topical formulation development of a novel thymidylate synthase inhibitor for the treatment of psoriasis", Int. J. Pharm., 1994; 105: 227-233; Ritschel, W. A., Hussain, A. S., "In vitro skin permeation of griseofulvin in rat and human skin from an ointment dosage form", Arzneimeittelforsch/Drug Res. 1988; 38: 1630-1632; Touitou, E., Levi-Schaffer, F., Shaco-Ezra, N., Ben-Yossef, R. and Fabin, B., "Enhanced permeation of theophylline through the skin and its effect on fibroblast proliferation", Int. J. Pharm., 1991; 70: 159-166; Watkinson, A. C., Hadgraft, J. and Bye, A., "Enhanced permeation of prostaglandin E2 through human skin in vitro", Int. j. Pharm., 1991; 74: 229-236; Rojas, J., Falson, F., Courraze, G., Francis, A., and Puisieux, F., "Optimization of binary and ternary solvent systems in the percutaneous absorption of morphine base", STP Pharma Sciences, 1991; 1: 71-75; Ritschel, W. A., Barkhaus, J K., "Use of absorption promoters to increase systemic absorption of coumarin from transdermal drug delivery systems", Arzneimeittelforsch/Drug Res. 1988; 38: 1774-1777.

Thus there remains a need to provide a pharmaceutically acceptable transdermal or transmucosal pharmaceutical formulation or drug delivery system that exhibits the advantages of both occlusive systems (high thermodynamic activity) and non-occlusive systems (low irritation and sensitization potential, and excellent skin tolerance) while overcoming the disadvantages of these systems. The novel transdermal or transmucosal pharmaceutical formulation of the present invention satisfies this need.

The present invention is directed to the transdermal administration of a nicotine compound and pharmaceutically acceptable salts thereof. The preferred nicotine compound is nicotine, a well know, highly characterized alkaloid that can be isolated from the dried leaves of Nicotiana tabacum. A variety of patents have disclosed nicotine-containing compositions, such as chewing gums, nicotine-impregnated dermal patches, nicotine inhalers and the like: see, e.g., U.S. Pat. Nos., 7,029,692, 6,995,265, 6,828,336, 6,676,959, 6,596,740, 6,479,076, the entire content of which are incorporated herein as reference. Nicotine, the primary alkaloid in tobacco products binds stereo-selectively to nicotinic-cholinergic receptors on autonomic ganglia, the adrenal medulla, neuromuscular junctions and in the brain. Nicotine exerts two effects, a stimulant effect exerted at the locus ceruleus and a reward effect in the limbic system. Intravenous administration of nicotine causes release of acetylcholine, norepinephrine, dopamine, serotonine, vasopressin, beta-endorphin and ACTH. Nicotine is a highly addictive substance. Nicotine also induces peripheral vasoconstriction, tachycardia and elevated blood pressure. Nicotine inhalers and patches are used to treat smoking withdrawal syndrome. Nicotine is classified as a stimulant of autonomic ganglia. Nicotine, or 1-methyl-2-(3-pyridyl)pyrrolidone, is an oily colourless or pale yellow liquid with a pyridine odour, a molecular weight of about 162, an octanol:water partition coefficient (log P) of about 1.2, a dissociation constant (pKa) of about 3.1, a solubility in water of about and a melting point of approximately $-79°$ C. Nicotine is miscible with water below 60° C. (See monograph of nicotin in Clarke's Analysis of Drugs and Poisons, ©Pharmaceutical Press 2005, the entire content of which is herein incorporated as reference). Nicotine is readily absorbed from the gastro-intestinal tract, the buccal mucosa, the respiratory tract, and intact skin, and widely distributed throughout the tissues. Nicotine undergoes extensive first-pass metabolism when administered orally, thus reducing the bioavailability. Oral bioavailability of nicotine is about 30%.

Nicotine numerous commercial uses include utilities such as a fumigant, an insecticide and the like. It is therapeutically valuable in the treatment of the smoking withdrawal syndrome. Nicotine has also been found therapeutically valuable in the treatment of other conditions involving release of dopamine such as attention deficit hyperactive disorder (ADHD), attention deficit disorder (ADD), Tourette's syndrome, schizophrenia, Alzheimer's disease, Parkinson's disease, anxiety and depression (see, e.g., U.S. Pat. Nos. 6,911, 475; 6,479,076; 6,034,079, 5,278,176); in the therapeutic angiogenesis and vasculogenesis (see, e.g., U.S. Pat. No. 6,417,205); in the treatment of inflammatory bowel disease (see, e.g., U.S. Pat. No. 6,166,044).

Several drug products containing nicotine are currently marketed (as of July 2006) in the US: see U.S. Food and Drug Administration, Center for Drug Evaluation and Research website, from where the excerpt table herein after is extracted:

| DRUG NAME | ACTIVE INGREDIENT | DOSAGE FORM | COMPANY |
| --- | --- | --- | --- |
| COMMIT | NICOTINE POLACRILEX | TROCHE/LOZENGE; ORAL | GLAXOSMITHKLINE CONS |
| HABITROL | NICOTINE | FILM, EXTENDED RELEASE; TRANSDERMAL | NOVARTIS |
| NICODERM CQ | NICOTINE | FILM, EXTENDED RELEASE; TRANSDERMAL | SANOFI AVENTIS US |
| NICORETTE | NICOTINE POLACRILEX | GUM, CHEWING; BUCCAL | GLAXOSMITHKLINE |

-continued

| DRUG NAME | ACTIVE INGREDIENT | DOSAGE FORM | COMPANY |
| --- | --- | --- | --- |
| NICORETTE (MINT) | NICOTINE POLACRILEX | GUM, CHEWING; BUCCAL | GLAXOSMITHKLINE |
| NICOTINE | NICOTINE | FILM, EXTENDED RELEASE; TRANSDERMAL | SANO |
| NICOTINE POLACRILEX | NICOTINE POLACRILEX | GUM, CHEWING; BUCCAL | PERRIGO |
| NICOTROL | NICOTINE | SPRAY, METERED; NASAL FILM, EXTENDED RELEASE; TRANSDERMAL INHALANT; ORAL | PHARMACIA AND UPJOHN |
| PROSTEP | NICOTINE | FILM, EXTENDED RELEASE; TRANSDERMAL | AVEVA |

However, the herein above drug products, and more particularly transdermal patches, are not free of drawbacks.

Inherently to the occlusive nature of the transdermal patches, nicotine transdermal systems are often reported to cause skin irritation. See, for instance, Greenland et al. in "A meta-analysis to assess the incidence of adverse effects associated with the transdermal nicotine patch", Drug Saf. 1998 April; 18(4):297-308: the meta-analysis represented a synthesis of data from 41 groups of nicotine patch recipients totaling 5501 patients, and 33 groups of placebo recipients totaling 3752 patients. The incidences of several minor adverse effects were clearly elevated among the nicotine-patch groups, especially localized skin irritation. See also Smith et al., in "Smoking cessation: a clinical study of the transdermal nicotine patch", J Am Osteopath Assoc. 1995 November; 95(11):655-6, 661-2. See also Frederikson et al., in "High dose transdermal nicotine therapy for heavy smokers: safety, tolerability and measurement of nicotine and cotinine levels", Psychopharmacology (Berl). 1995 December; 122(3):215-22. See also Sudan in "Nicotine skin patch treatment and adverse reactions: skin irritation, skin sensitization, and nicotine as a hapten", J Clin Psychopharmacol. 1995 April; 15(2):145-6. See also Andersen et al. in "Chemical and pharmacologic skin irritation in man: a reflectance spectroscopic study", Contact Dermatitis. 1991 November; 25(5): 283-9. See also Gupta et al., in "Bioavailability and absorption kinetics of nicotine following application of a transdermal system", Br J Clin Pharmacol. 1993 September; 36(3):221-7.

Skin irritation caused by nicotine transdermal patches is caused by the intrinsic skin-irritant properties of the drug itself, but also by the occlusive nature of the patch (which prevents the skin from normally "breathing"), and also by the adhesives used to maintain the skin attached to the skin. Indeed, patients are often asked to change regularly the change of application of the patch in order to prevent/minimize such unpleasant local skin reactions Besides drawbacks commonly associated with transdermal patches, nicotine transdermal patches do also present inherent drawbacks. For instance, Klemsdal et al. ("Physical exercise increases plasma concentrations of nicotine during treatment with a nicotine patch.", in Br J Clin Pharmacol. 1995 June; 39(6):677-9) have demonstrated that because of the occlusion, mean plasma nicotine concentration increased from 9.8 to 11.0 ng ml-1 (P=0.015) during physical exercise, and fell non-significantly from 10.5 to 10.2 ng ml-1 during rest. The increase in plasma nicotine concentration during exercise may be related to an exercise-induced increase in blood flow in the patch area. It is believed that such variations of nicotine mean plasma concentration following physical exercise is minimized and/or prevented if applying non-occlusive nicotine dosage forms.

Prather et al. in "Nicotine pharmacokinetics of Nicoderm (nicotine transdermal system) in women and obese men compared with normal-sized men", J Clin Pharmacol. 1993 July; 33(7):644-9, reported that nicotine Cmax and AUC values were significantly lower in obese compared with normal-sized men, and that nicotine AUC was strongly correlated to body weight and body mass index. It is believed that transdermal semi-solid dosage forms, such as transdermal gels, would minimize such variations of nicotine bioavailability since they offer a greater dosing flexibility by simply increasing or decreasing the dose of gel to be rubbed on the skin.

Woolf et al. reported that 18 children had bitten, chewed, or swallowed part of a transdermal nicotine patch. All four commercial brands of transdermal nicotine patch were represented; no brand was associated with more symptoms or an increased severity of illness. It is also highlighted that pediatric exposures to patches containing other medications, such as clonidine, have been previously reported in the past (see electronic article "Childhood Poisoning Involving Transdermal Nicotine Patches", Pediatrics Vol. 99 No. 5 May 1997, p. e4). Indeed, patient information leaflets of transdermal patches very often emphasize the disposal guidelines of patches, which should be folded in half and thrown away out of the reach of children.

U.S. Pat. No. 4,597,961 describes an occlusive pad comprising a reservoir for liquid nicotine base to be affixed to the skin in a variety of places.

U.S. Pat. No. 5,230,896 describes a transdermal delivery system for nicotine which comprises a nicotine base, an acrylate polymer adhesive, a stabilizer and a polyester film backing.

U.S. Pat. No. 5,603,947 describes a skin or buccal patch for providing nicotine replacement therapy which comprises a matrix type laminated composite in which the matrix is composed of a mixture of nicotine in a polymer.

U.S. Pat. No. 5,633,008 describes a method of administering nicotine transdermally in which a nicotine patch, capable of administering nicotine for at least 16 hours at rates that are efficacious in smoking cessation therapy, is applied in the morning upon waking and removed prior to sleep.

U.S. Pat. No. 5,783,207 describes a nicotine-containing dosage-form comprising an attached holder member which may be used to manipulate the dosage form within the mouth of the patient.

U.S. Pat. No. 5,935,604 describes a nasal drug delivery composition comprising a complex of an ion-exchange material with nicotine or a pharmacologically-acceptable salt or derivative thereof.

U.S. Pat. No. 6,165,497 describes subsaturated rate-controlled transdermal nicotine therapeutic delivery systems which utilize an in-line adhesive to maintain the systems on the skin.

U.S. Pat. No. 6,479,076 describes compositions containing nicotine and an uncrosslinked, water-insoluble vinylpyrrolidone copolymer to be applied on the skin of patients.

U.S. Pat. No. 6,596,740 describes nicotine nasal spray compositions.

U.S. Pat. No. 6,676,959 describes nicotine-containing oral solid pharmaceutical compositions essentially comprising apolar, polar and surface-active components and giving a rapid transmucosal absorption.

U.S. Pat. No. 6,828,336 describes nicotine-containing, controlled release composition in powder form for oral administration from which nicotine release rate is not less than 70% over a 10 minute period.

U.S. Pat. No. 7,029,692 describes transdermal nicotine patches containing monoterpene ketones as odour-improving substances.

No admission is made that any reference, including any patent or patent document, cited in this specification constitutes prior art. In particular, it will be understood that, unless otherwise stated, reference to any document herein does not constitute an admission that any of these documents forms part of the common general knowledge in the art in United States of America or in any other country. The discussion of the references states what their authors assert, and the applicant reserves the right to challenge the accuracy and pertinency of any of the documents cited herein.

In view of the aforementioned, there remains a need to provide a pharmaceutically acceptable transdermal or transmucosal pharmaceutical formulation or drug delivery system containing nicotine or pharmaceutically acceptable salts thereof that exhibits the advantages of both occlusive systems (high thermodynamic activity) and non-occlusive systems (low irritation and sensitization potential, and excellent skin tolerance) while overcoming the disadvantages of these systems. The novel transdermal or transmucosal pharmaceutical formulation of the present invention satisfies this need.

The formulations of the present invention as described herein below provide a number of advantages for the transdermal delivery of nicotine and its derivatives. These include, but are not limited to, continuous, steady-state delivery, which can provide sustained blood levels of the agent(s).

SUMMARY OF THE INVENTION

In one aspect, the present invention relates to non occlusive compositions (for example, a gel) for pharmaceutical drug delivery. In one embodiment, the composition may be formulated to be suitable for transdermal application. The composition typically comprises a therapeutically effective amount of nicotine or a pharmaceutically acceptable salt thereof. A preferred salt is the hydrogen tartrate. Further, the composition may be a gel. The gel typically comprises a primary vehicle comprising a mixture of water and at least one short-chain alcohol (i.e., a hydroalcoholic vehicle), one or more antioxidant; and one or more buffering agent. The apparent pH of the gel is usually between about pH 4.5 and about pH 8.5, and the gel is adapted for application to the surface of skin. The compositions for pharmaceutical delivery may include further components as described herein, for example, the hydroalcoholic vehicle may further comprise additional solvent(s), antioxidant(s), cosolvent(s), penetration enhancer(s), buffering agent(s), and/or gelling agent(s).

Preferred embodiments of the present invention are gel formulations for non-occlusive therapeutic, transdermal applications.

The formulations of the present invention may be provided, for example, in unit dose container(s) or multiple dose containers.

In another aspect the present invention comprises a composition for pharmaceutical drug delivery. Such compositions may, for example, comprise a therapeutically effective amount of nicotine, or a pharmaceutically acceptable salt thereof, a hydroalcoholic vehicle, and at least one buffering agent. In such compositions the apparent pH of the composition is between about pH 4.5 and about pH 8.5. Further, the transdermal flux of the nicotine, in the hydroalcoholic vehicle of the present invention is greater than the transdermal flux of an equal concentration of nicotine in an aqueous solution of essentially equivalent pH over an essentially equivalent time period, wherein the skin acts as the flux rate controlling membrane.

In yet another aspect the present invention comprises a composition for pharmaceutical drug delivery. Such compositions may, for example, comprise a therapeutically effective amount of a nicotine compound, or a pharmaceutically acceptable salt thereof, in a hydroalcoholic vehicle. In such compositions the transdermal flux of the nicotine in the hydroalcoholic vehicle of the present invention is independent from the apparent pH of said compositions.

The above-described compositions for pharmaceutical delivery may include further components as described herein, for example, the hydroalcoholic vehicle may further comprise additional solvent(s), antioxidant(s), cosolvent(s), penetration enhancer(s), buffering agent(s), and/or gelling agent (s).

The compositions of the present invention may be used, for example, for transdermal applications including application to skin and mucosal tissue (for example, intranasally, intrabucally, as an ovule or as a suppository).

In yet another aspect, the present invention includes dosage forms for pharmaceutical delivery of a drug, preferably a nicotine compound such as, for example, nicotine. In one embodiment, the dosage form is configured to provide steady-state delivery of nicotine with once-a-day dosing.

In a further aspect, the present invention includes methods of manufacturing the compositions described herein for pharmaceutical drug delivery.

In another aspect, the present invention includes methods for administering an active agent to a subject in need thereof. For example, the method may comprise providing a composition of the present invention for transdermal, pharmaceutical delivery of nicotine. Nicotine, and pharmaceutical salts thereof, can be used for the treatment of a variety of conditions including, but not limited to, smoking cessation, inflammatory bowel disease, and neurological disorders. Exemplary neurological disorders include, but are not limited to, anxiety, depression, schizophrenia, Alzheimer's Disease, Parkinson's Disease, Restless Legs Syndrome, Tourette's Syndrome, Chronic Tic Disorder, Essential Tremor, and Attention Deficit Hyperactivity Disorder.

These and other embodiments of the present invention will readily occur to those of ordinary skill in the art in view of the disclosure herein.

BRIEF DESCRIPTION OF THE DRAWING FIGURES

Figure 1A:
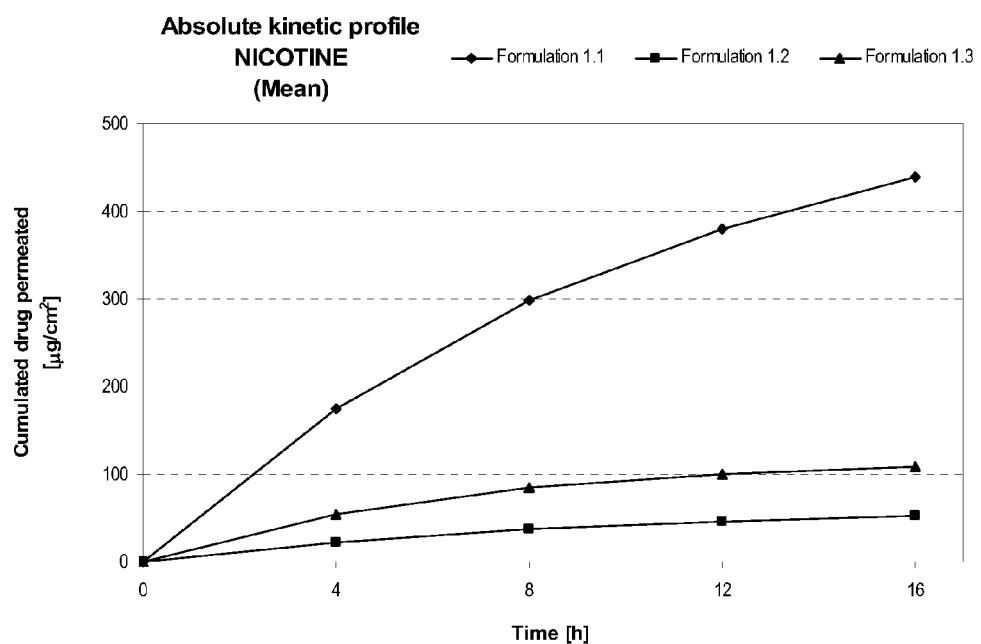
FIG. 1A shows data for the absolute kinetic delivery profile of nicotine delivery over the 16 hour permeation using the formulations described in Example 1.

FIG. 1Abis shows data for the absolute kinetic delivery profile of nicotine delivery over the 16 hour permeation using the formulations described in Example 1bis.

Figure 2A:
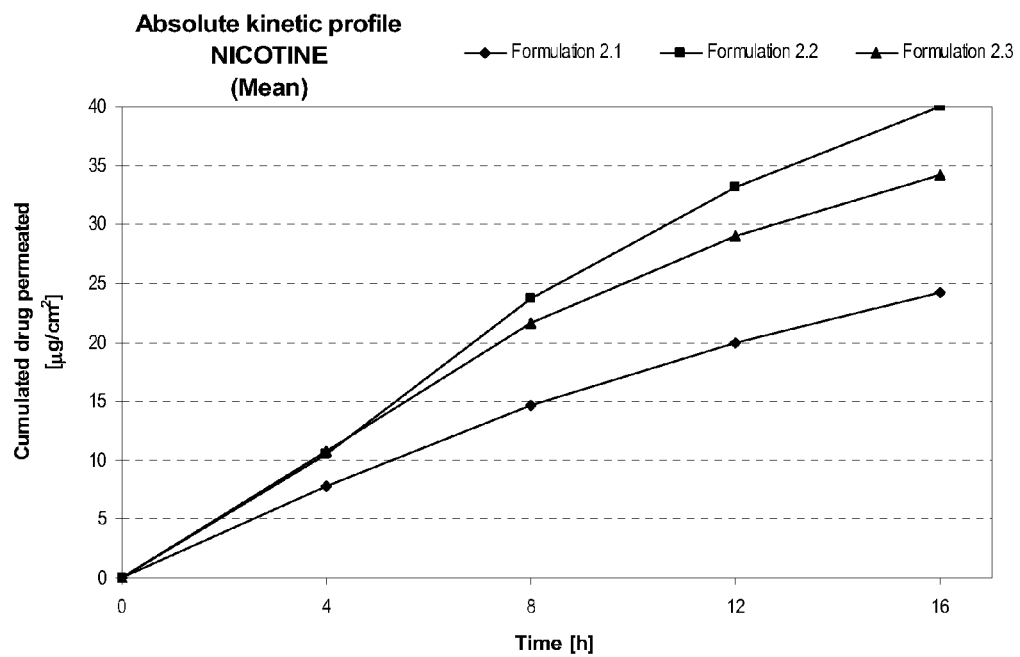

FIG. 2Abis shows data for flux results from the permeation analysis using the formulations in described in Example 1bis.

FIG. 2A shows data for the absolute kinetic delivery profile of nicotine delivery over the 16 hour permeation using the formulations described in Example 2.

Figure 2B:
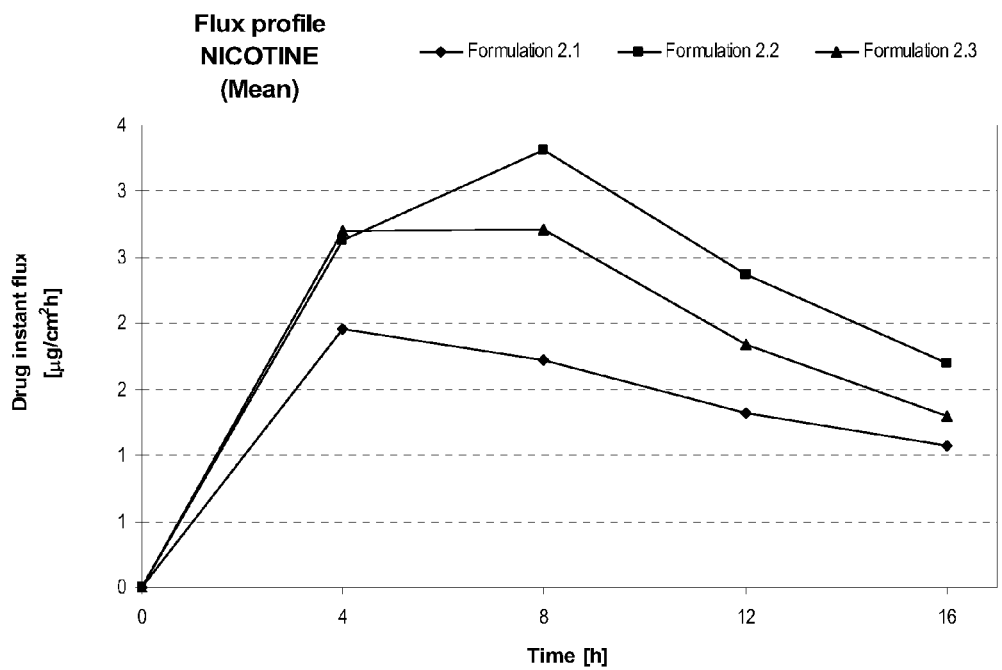

FIG. 2B shows data for flux results from the permeation analysis using the formulations in described in Example 2.

Figure 3A:
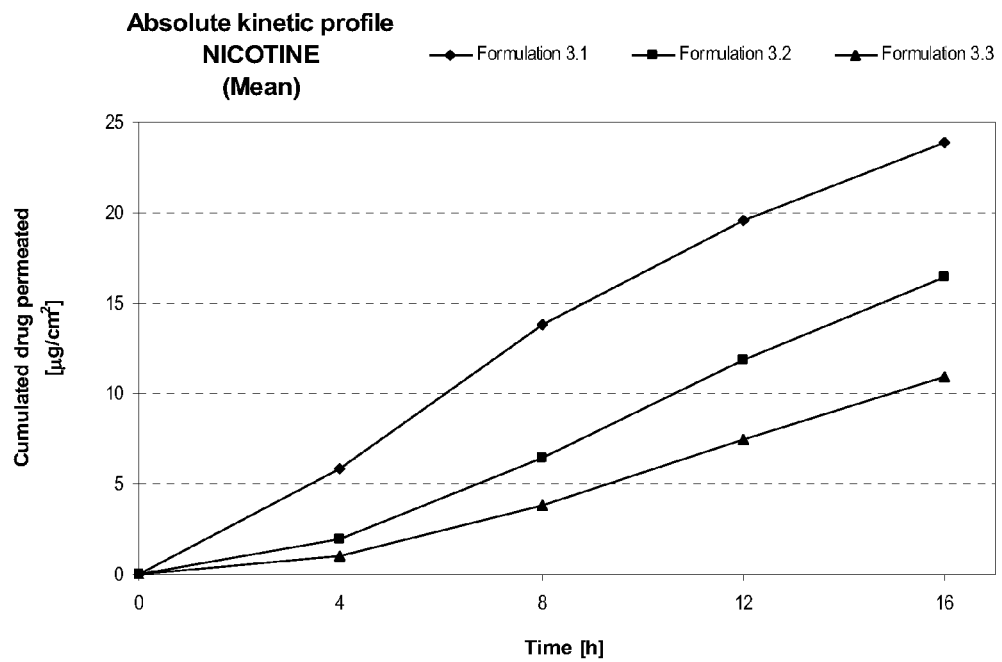

FIG. 3A shows data for the absolute kinetic delivery profile of nicotine delivery over the 16 hour permeation using the formulations described in Example 3.

Figure 3B:
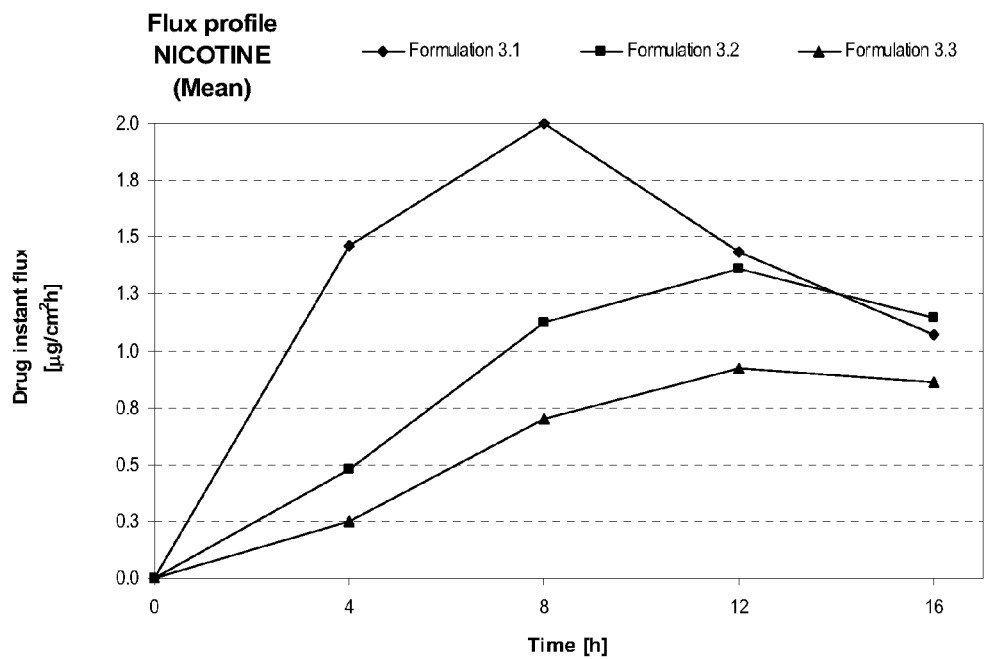

FIG. 3B shows data for flux results from the permeation analysis using the formulations in described in Example 3.

Figure 4A:
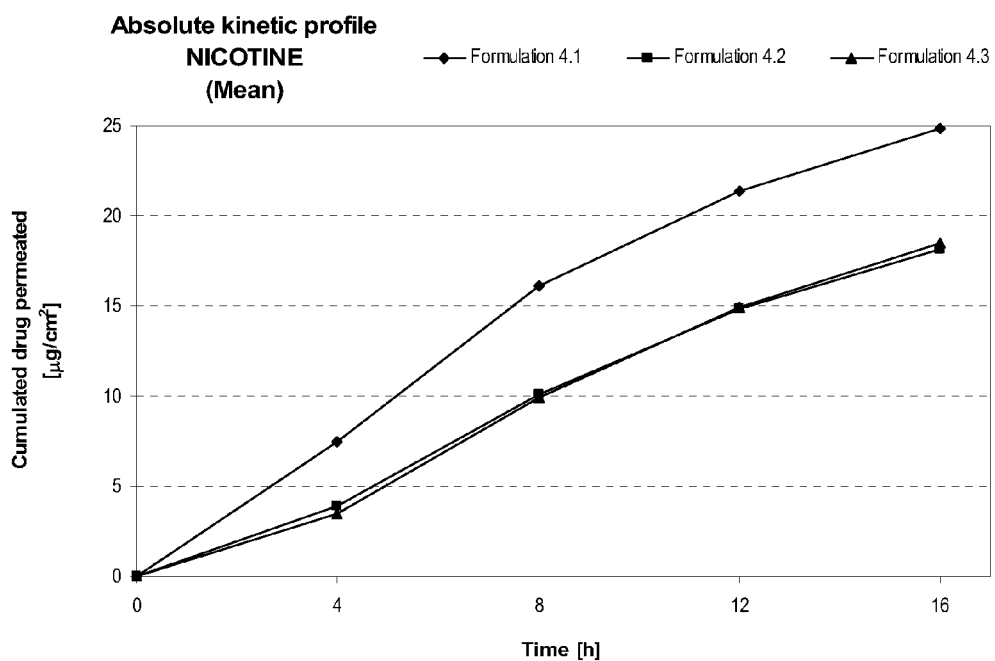

FIG. 4A shows data for the absolute kinetic delivery profile of nicotine delivery over the 16 hour permeation using the formulations described in Example 4.

Figure 4B:
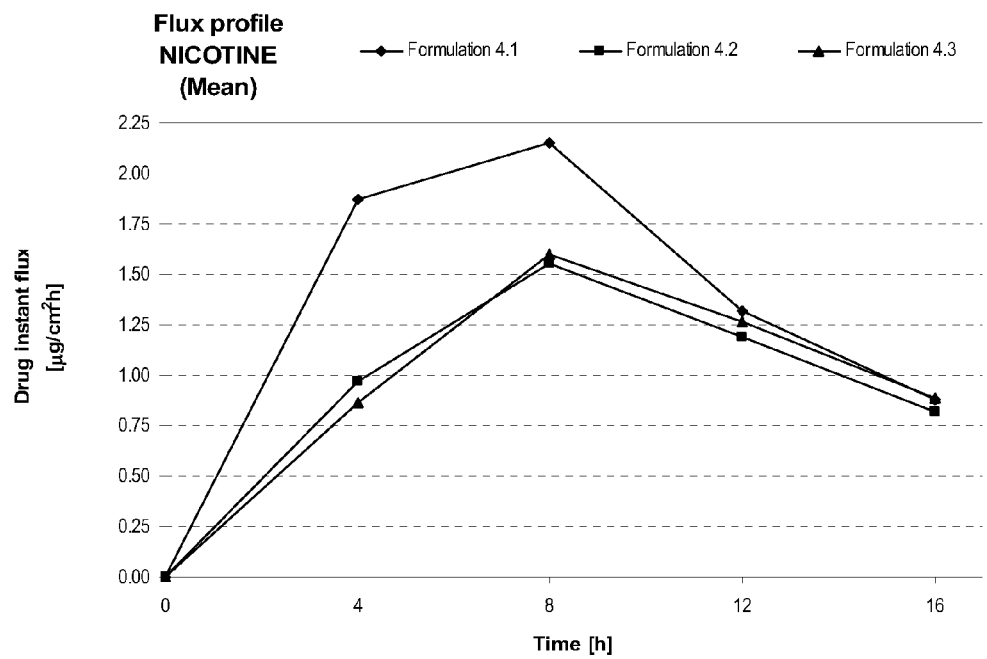

FIG. 4B shows data for flux results from the permeation analysis using the formulations in described in Example 4.

Figure 5A:
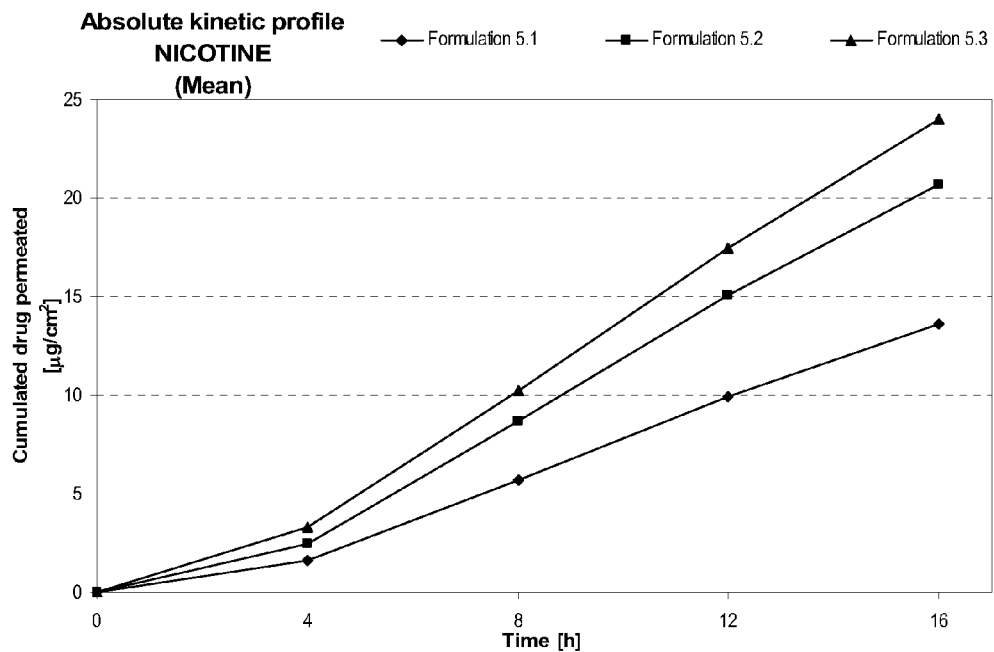

FIG. 5A shows data for the absolute kinetic delivery profile of nicotine delivery over the 16 hour permeation using the formulations described in Example 5.

Figure 5B:
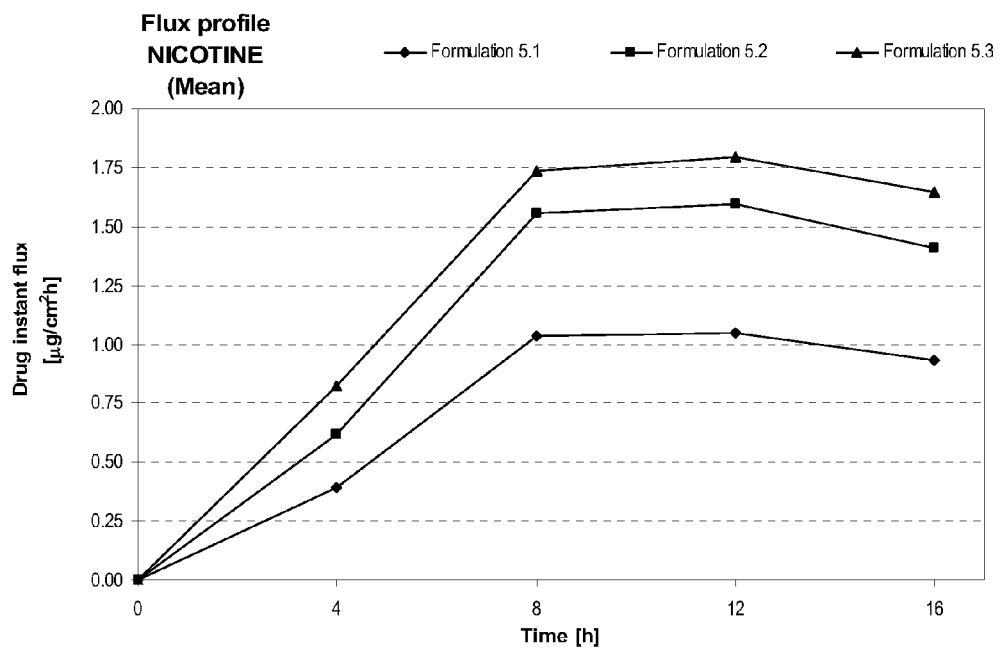

FIG. 5B shows data for flux results from the permeation analysis using the formulations in described in Example 5.

Figure 5C:
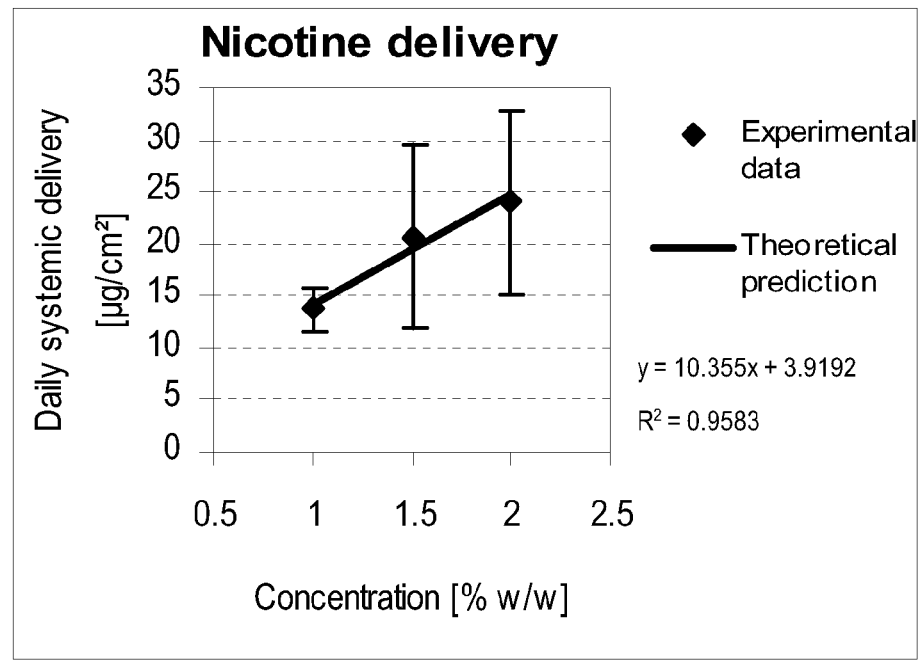

FIG. 5C shows theoretical predictions and experimental data of nicotine delivery as a function of nicotine dose concentration in the formulations described in Example 5.

Figure 6A:
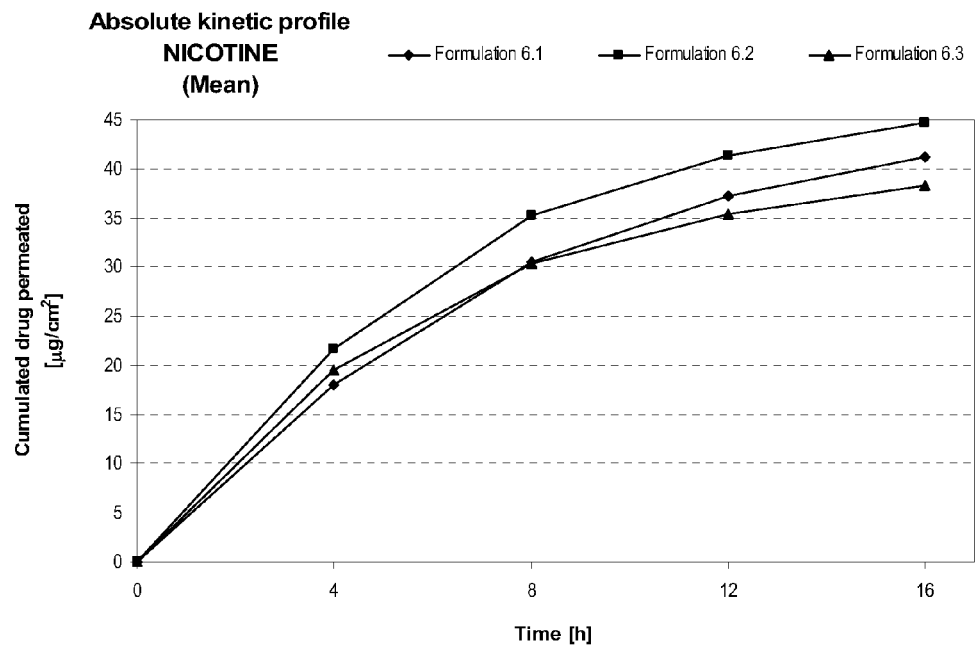

FIG. 6A shows data for the absolute kinetic delivery profile of nicotine delivery over the 16 hour permeation using the formulations described in Example 6.

Figure 6B:
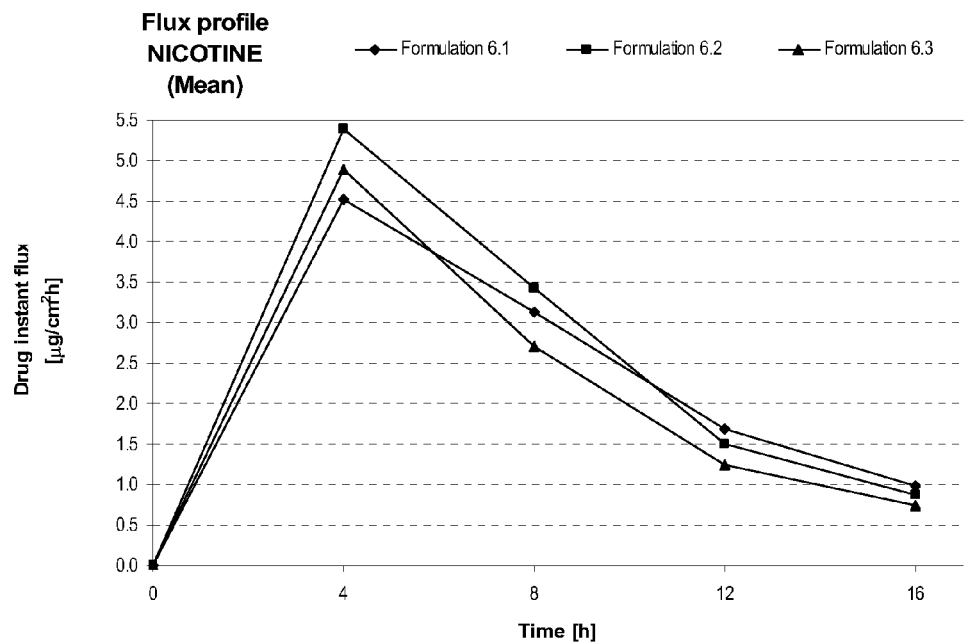

FIG. 6B shows data for flux results from the permeation analysis using the formulations in described in Example 6.

Figure 7A:
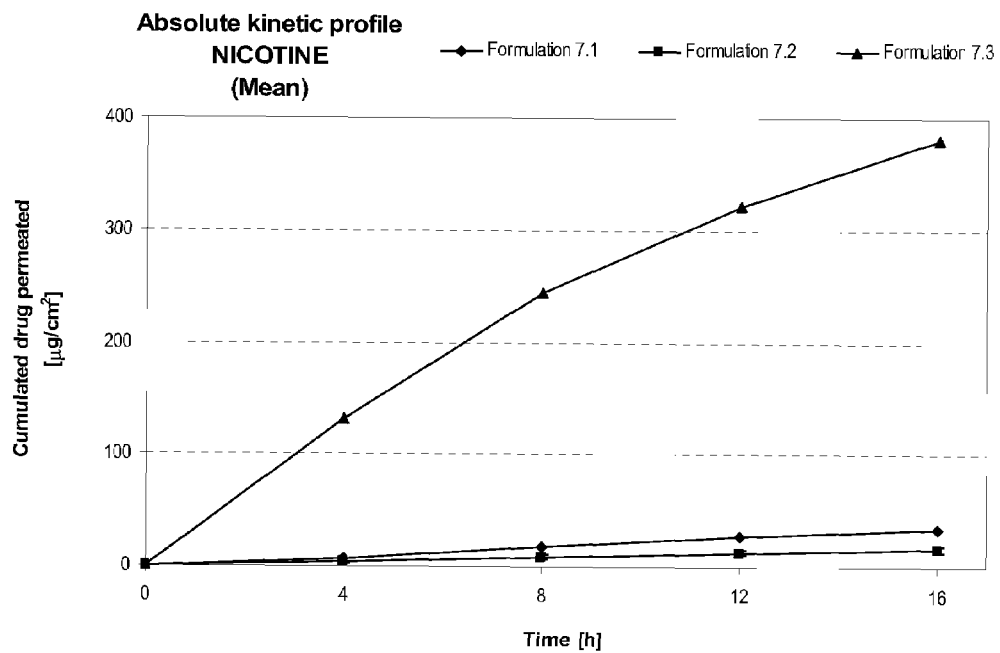

FIG. 7A shows data for the absolute kinetic delivery profile of nicotine delivery over the 16 hour permeation using the formulations described in Example 7.

Figure 7B:
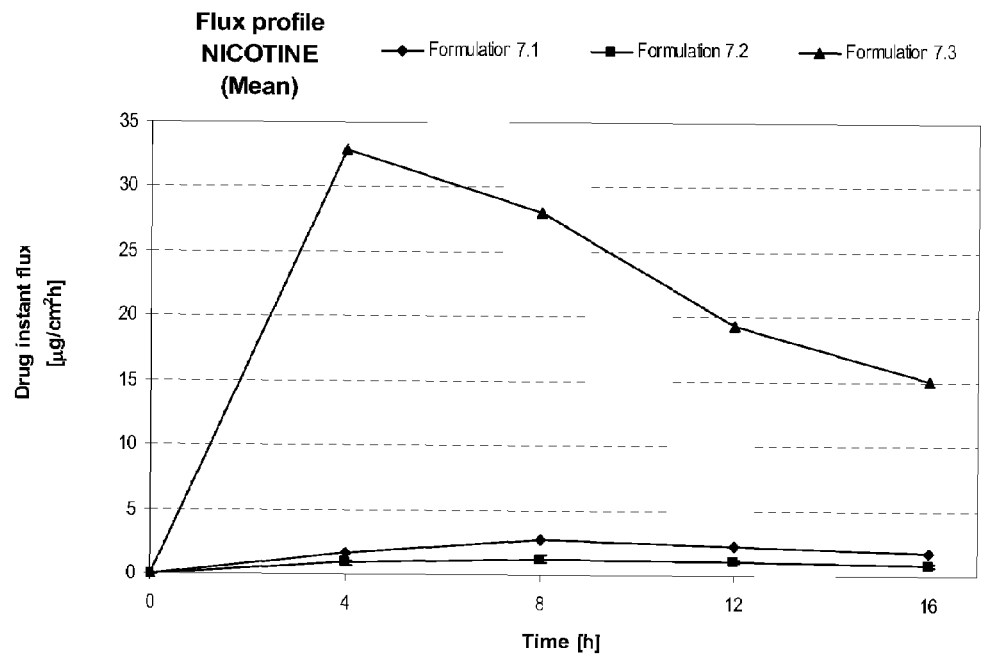

FIG. 7B shows data for flux results from the permeation analysis using the formulations in described in Example 7.

DETAILED DESCRIPTION OF THE PREFERRED EMBODIMENTS

All patents, publications, and patent applications cited in this specification are herein incorporated by reference as if each individual patent, publication, or patent application was specifically and individually indicated to be incorporated by reference in its entirety for all purposes.

It is to be understood that the terminology used herein is for the purpose of describing particular embodiments only, and is not intended to be limiting. As used in this specification, description of specific embodiments of the present invention, and any appended claims, the singular forms "a," "an" and "the" include plural referents unless the context clearly dictates otherwise. Thus, for example, reference to "a cosolvent" includes two or more cosolvents, mixtures of cosolvents, and the like, reference to "a compound" includes one or more compounds, mixtures of compounds, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "dosage form" as used herein refers to a pharmaceutical composition comprising an active agent, such as nicotine, and optionally containing inactive ingredients, e.g., pharmaceutically acceptable excipients such as suspending agents, surfactants, disintegrants, binders, diluents, lubricants, stabilizers, antioxidants, osmotic agents, colorants, plasticizers, coatings and the like, that may be used to manufacture and deliver active pharmaceutical agents.

The term "gel" as used herein refers to a semi-solid dosage form that contains a gelling agent in, for example, an aqueous, alcoholic, or hydroalcoholic vehicle and the gelling agent imparts a three-dimensional cross-linked matrix ("gellified") to the vehicle. The term "semi-solid" as used herein refers to a heterogeneous system in which one solid phase is dispersed in a second liquid phase.

The pH measurements for formulations and compositions described herein, wherein the formulations or compositions do not comprise a predominantly aqueous environment, are more aptly described as "apparent pH" values as the pH values are not determined in a predominantly aqueous environment. In such cases, the influence of, for example, organic solvents on the pH measurement may result in a shift of pH relative to a true aqueous environment.

The term "carrier" or "vehicle" as used herein refers to carrier materials (other than the pharmaceutically active ingredient) suitable for transdermal administration of a pharmaceutically active ingredient. A vehicle may comprise, for example, solvents, cosolvents, permeation enhancers, pH buffering agents, antioxidants, gelling agents, additives, or the like, wherein components of the vehicle are nontoxic and do not interact with other components of the total composition in a deleterious manner.

The phrase "non-occlusive, transdermal drug delivery" as used herein refers to transdermal delivery methods or systems that do not occlude the skin or mucosal surface from contact with the atmosphere by structural means, for example, by use of a patch device, a fixed application chamber or reservoir, a backing layer (for example, a structural component of a device that provides a device with flexibility, drape, or occlusivity), a tape or bandage, or the like that remains on the skin or mucosal surface for a prolonged period of time. Non-occlusive, transdermal drug delivery includes delivery of a drug to skin or mucosal surface using a topical medium, for example, creams, ointments, sprays, solutions, lotions, gels, and foams. Typically, non-occlusive, transdermal drug delivery involves application of the drug (in a topical medium) to skin or mucosal surface, wherein the skin or mucosal surface to which the drug is applied is left open to the atmosphere.

The term "transdermal" delivery, as used herein refers to both transdermal (and "percutaneous") and transmucosal administration, that is, delivery by passage of a drug through a skin or mucosal tissue surface and ultimately into the bloodstream.

The phrase "therapeutically effective amount" as used herein refers to a nontoxic but sufficient amount of a drug, agent, or compound to provide a desired therapeutic effect, for example, one or more doses of nicotine that will be effective in relieving symptoms of smoking cessation, inflammatory bowel disease, neurological disorder (e.g., anxiety, depression, schizophrenia, Alzheimer's Disease, Parkinson's Disease, Restless Legs Syndrome, Tourette's Syndrome, Chronic Tic Disorder, Essential Tremor, and Attention Deficit Hyperactivity Disorder).

The term "nicotine compound" as used herein refers to any of the conventional nicotine compounds, including nicotine, nicotine free base, pharmaceutically acceptable salts thereof, as well as mixtures of free base and salt forms. One example of a pharmaceutically acceptable salt of nicotine is the hydrogen tartrate salt (or, whose systematic name is pyridine, 3-(1-methyl-2-pyrrolidinyl)-, (S)—, (R—(R*,R*))-2,3-dihydroxybutanedioate (1:2), or nicotine, tartrate (1:2), or nicotine dihydrogen ditartrate), which has an empirical formula of $C_{10}H_{14}N_2, 2\ C_4H_6O_6$. The molecular weight of nicotine hydrogen tartrate is approximately 462. The structure of nicotine hydrogen tartrate is as follows:

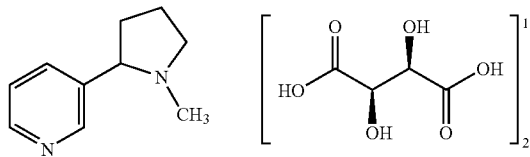

Another example of a pharmaceutically acceptable salt of nicotine is nicotine, tartrate, hydrate (1:2:2) (synonym: nicotine bitartrate dihydrate), which has an empirical formula of $C_{10}H_{14}N_2, 2\ C_4H_6O_6, 2\ H_2O$. The molecular weight of nicotine hydrogen tartrate is approximately 498. As used herein after, the phrase "nicotine bitartrate dihydrate" and "nicotine hydrogen tartrate" are totally interchangeable.

The phrase "nicotine free base equivalent" (nicotine FBE) as used herein typically refers to the actual amount of the nicotine molecule in a formulation, that is, independent of the amount of the associated salt forming compound that is present in a nicotine salt. The phrase nicotine free base equivalent may be used to provide ease of comparison between formulations made using nicotine free base or any of a number of nicotine salts to show the amount of active ingredient (e.g., nicotine) that is present in the formulation. For example, free base nicotine has a molecular weight of approximately 162. Nicotine hydrogen tartrate has a molecular weight of approximately 462 of which approximately 300 of the molecular weight is attributed to tartaric acid. The molecular weight ratio of nicotine hydrogen tartrate to free base nicotine is 2.85. Accordingly, when nicotine hydrogen tartrate is present in a formulation at 4.28 weight percent this corresponds to a nicotine free base equivalent of 1.50 weight percent (4.28/2.85=1.50). Nicotine bitartrate dihydrate has a molecular weight of approximately 498 of which approximately 336 of the molecular weight is attributed to tartaric acid and water. The molecular weight ratio of nicotine bitartrate dihydrate to free base nicotine is 3.07. Accordingly, when nicotine bitartrate dihydrate is present in a formulation at 4.6 weight percent this corresponds to a nicotine free base equivalent of 1.50 weight percent (4.6/3.07=1.50).

The term "nicotine pharmaceutically acceptable salts" as used herein refers to formation of salts with acceptable salt formers such as, but not limited to, hydrochloride, sulphate, tosylate, mesylate, napsylate, besylate, maleate, phosphate, salicylate, tartrate, lactate, citrate, benzoate, succinate, acetate, pivalate, oxalate, picrate, phthalate, etc . . . . As used herein, "nicotine pharmaceutically acceptable salts" can designate anhydrous salts or hydrated salts. Nicotine hydrated salts can be mono hydrated salts or polyhydrated salts. The term "nicotine pharmaceutically acceptable salts" as used herein also refers to formation of salts with polymers such as, but not limited to, methacrylic acid polymers, polyvinylpyrrolidone, polyvinyl alcohol, cyclodextrins, etc . . . .

The phrase "short-chain alcohol" as used herein refers to a $C_2$-$C_4$ alcohol, for example, ethanol, propanol, butanol, isopropanol, and/or mixtures of thereof.

The phrase "volatile solvent" refers to a solvent that changes readily from solid or liquid to a vapor, and that evaporates readily at normal temperatures and pressures. Examples of volatile solvents include, but are not limited to, ethanol, propanol, butanol, isopropanol, and/or mixtures thereof. The term "non-volatile solvent" as used herein refers to a solvent that does not change readily from solid or liquid to a vapor, and that does not evaporate readily at normal temperatures and pressures. Examples of non-volatile solvents include, but are not limited to, propylene glycol, glycerin, liquid polyethylene glycols, polyoxyalkylene glycols, and/or mixtures thereof. Stanislaus, et al., (U.S. Pat. No. 4,704,406) defined "volatile solvent" as a solvent whose vapor pressure is above 35 mm Hg when skin temperature is 32° C., and a "non-volatile" solvent as a solvent whose vapor pressure is below 10 mm Hg at 32° C. skin temperature. Solvents used in the practice of the present invention are typically physiologically compatible and used at non-toxic levels.

The phrase "monoalkylether of diethylene glycol" means a chemical having general formula $C_4H_{10}O_3(C_nH_{2n+1})$ wherein n=1-4. Further, the term "glycol" encompasses a broad range of chemicals including but not limited to propylene glycol, dipropylene glycol, butylene glycol, and polyethyleneglycols having general formula $CH_2OH(CH_2OH)_nCH_2OH$ wherein n (number of oxyethylene groups)=4-200.

The phrase "permeation enhancer" or "penetration enhancer" as used herein refers to an agent that improves the rate of transport of a pharmacologically active agent (e.g., nicotine) across the skin or mucosal surface. Typically a penetration enhancer increases the permeability of skin or mucosal tissue to a pharmacologically active agent. Penetration enhancers, for example, increase the rate at which the pharmacologically active agent permeates through skin and enters the bloodstream. Enhanced permeation effected through the use of penetration enhancers can be observed, for example, by measuring the flux of the pharmacologically active agent across animal or human skin as described in the Examples herein below. An "effective" amount of a permeation enhancer as used herein means an amount that will provide a desired increase in skin permeability to provide, for example, the desired depth of penetration of a selected compound, rate of administration of the compound, and amount of compound delivered.

The phrase "contamination" or "transfer" as used herein means the unintended presence of harmful substances in individuals or surfaces by direct contact between individuals, between surfaces, or between individuals and surfaces (and reciprocally).

The phrase "synergy", "synergism", "synergistic effect" or "synergistic action" as used herein means an effect of the interaction of the actions of two agents such that the result of the combined action is greater than expected as a simple additive combination of the two agents acting separately.

The phrase "modulate", "regulate" or "control" as used herein means to adjust, or maintain, with respect to a desired rate, degree, or condition, as to adjust permeation rate, crystallization speed, and repartition of an active pharmaceutical ingredient in the layers of the skin.

The phrase "effective" or "adequate" permeation enhancer or combination as used herein means a permeation enhancer or a combination that will provide the desired increase in skin permeability and correspondingly, the desired depth of penetration, rate of administration, and amount of drug delivered.

The phrase "thermodynamic activity" of a substance means the energy form involved in skin permeation of this substance. The chemical potential of a substance is defined in thermodynamics as the partial molar free energy of the substance. The difference between the chemical potentials of a drug outside and inside the skin is the energy source for the skin permeation process.

The phrase "stratum corneum" as used herein refers to the outer layer of the skin. The stratum corneum typically comprises layers of terminally differentiated keratinocytes (made primarily of the proteinaceous material keratin) arranged in a brick and mortar fashion wherein the mortar comprises a lipid matrix (containing, for example, cholesterol, ceramides, and long chain fatty acids). The stratum corneum typically creates the rate-limiting barrier for diffusion of the active agent across the skin.

The phrase "intradermal depot" as used herein refers to a reservoir or deposit of a pharmaceutically active compound within or between the layers of the skin (e.g., the epidermis, including the stratum corneum, dermis, and associated subcutaneous fat), whether the pharmaceutically active compound is intracellular (e.g., within keratinocytes) or intercellular.

The term "subject" as used herein refers to any warm-blooded animal, particularly including a member of the class Mammalia such as, without limitation, humans and non human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex.

The term "sustained release" as used herein refers to predetermined continuous release of a pharmaceutically active agent to provide therapeutically effective amounts of the agent over a prolonged period. In some embodiments of the present invention, the sustained release occurs at least in part from an intradermal depot of a pharmaceutically active compound.

The term "prolonged period" as used herein typically refers to a period of at least about 12 hours, more preferably at least about 18 hours and more preferably at least about 24 hours.

The term "sustained release dosage form" as used herein refers to a dosage form that provides an active agent, e.g., nicotine, substantially continuously for several hours, typically for a period of at least about 12 to about 24 hours.

The term "delivery rate" as used herein refers to the quantity of drug delivered, typically to plasma, per unit time, for example, nanograms of drug released per hour (ng/hr) in vivo.

In the context of plasma blood concentration of active agent, the term "C" as used herein refers to the concentration of drug in the plasma of a subject, generally expressed as mass per unit volume, typically nanograms per milliliter (this concentration may be referred to as "plasma drug concentration" or "plasma concentration" herein which is intended to be inclusive of drug concentration measured in any appropriate body fluid or tissue). The plasma drug concentration at any time following drug administration is typically referred to as Ctime as in C10h or C20h, etc. The term "Cmax" refers to the maximum observed plasma drug concentration following administration of a drug dose, and is typically monitored after administration of a first dose and/or after steady-state delivery of the drug is achieved. The following terms are used herein as follows: "Cavg" refers to average observed plasma concentration typically at steady state, Cavg at steady state is also referred to herein as "Css"; "Cmin" refers to minimum observed plasma concentration typically at steady state.

The term "Tmax" as used herein refers to the time to maximum plasma concentration and represents the time that elapses between administration of the formulation and a maximum plasma concentration of drug (i.e., a peak in a graph of plasma concentration vs. time). Tmax values may be determined during an initial time period (for example, related to administration of a single dose of the drug) or may refer to the time period between administration of a dosage form and the observed maximum plasma concentration during steady state.

The term "steady state" as used herein refers to a pattern of plasma concentration versus time following consecutive administration of a constant dose of active agent at predetermined intervals (for example, once-a-day dosing). During "steady state" the plasma concentration peaks and plasma concentration troughs are substantially the same within each dosing interval.

One of ordinary skill in the art appreciates that plasma drug concentrations obtained in individual subjects will vary due to inter-subject variability in many parameters affecting, for example, drug absorption, distribution, metabolism, and excretion. Accordingly, mean values obtained from groups of subjects are typically used for purposes of comparing plasma drug concentration data and for analyzing relationships between in vitro dosage assays and in vivo plasma drug concentrations.

Before describing the present invention in detail, it is to be understood that this invention is not limited to particular embodiments described herein, for example, particular solvent(s), antioxidant(s), cosolvent(s), penetration enhancer(s), buffering agent(s), and/or gelling agent(s), and the like, as use of such particulars may be selected in view of the teachings of the present specification by one of ordinary skill in the art. It is also to be understood that the terminology used herein is for the purpose of describing particular embodiments of the invention only, and is not intended to be limiting.

In one aspect, the present invention relates to a gel composition for pharmaceutical drug delivery. The gel may be formulated to be suitable for transdermal application, for example, transcutaneous and/or transmucosal applications. The gel typically comprises a therapeutically effective amount of nicotine or a pharmaceutically acceptable salt thereof. The gel typically comprises a primary vehicle comprising a mixture of water and at least one short-chain alcohol, a monoalkylether of diethylene glycol, a glycol, one or more antioxidant; and one or more buffering agent, wherein (i) the pH of the gel is between about pH 4.5 and about pH 8.5, and (ii) the gel is suitable for application to the surface of skin of a subject. In one embodiment, the nicotine is free base nicotine. In other embodiments, the nicotine is a pharmaceutically acceptable salt of nicotine (e.g., nicotine hydrogen tartrate). A preferred concentration range of nicotine is about 0.05 to about 5 weight percent of nicotine free base equivalents, more preferred is a concentration of about 1 to about 2 weight percent of nicotine free base equivalents.

The short-chain alcohol in formulations of the present invention may be, for example, ethanol, propanol, butanol, isopropanol, and mixtures thereof. A preferred concentration range of the short-chain alcohol, for example, ethanol, is a concentration of about 5 to about 75 weight percent where the water is present at a concentration of about 10 to about 60 weight percent. Water can be added quantum sufficiat (q.s.) so amounts may vary as can be determined by one of ordinary skill in the art in view of the teachings of the present specification. A more preferred concentration range of the short-chain alcohol, for example, ethanol, is about 40 to about 60 weight percent where the water is present at a concentration of about 10 to about 40 weight percent.

The gel formulations of the present invention further comprise a combination of a monoalkylether of diethylene glycol (for example mono ethyl ether of diethylene glycol) and a pharmaceutically acceptable glycol. In one embodiment the glycol is propylene glycol. A preferred concentration range of the monoalkylether of diethylene glycol and of the pharmaceutically acceptable glycol is a concentration of about 1 to about 30 weight percent, more preferred is a concentration of about 2.5 to about 20 weight percent. More preferred gel formulations of the present invention comprise combination wherein the monoalkylether of diethylene glycol to the pharmaceutically acceptable glycol ratio ranges from about 10:1 to 2:1 and from 1:2 to 1:10, and wherein the monoalkylether of diethylene glycol and the pharmaceutically acceptable glycol are present in combination in an amount of not less than 15 weight percent and not more than 60 weight percent of the total composition.

Further, the gel formulations of the present invention may further comprise a gelling or thickening agent(s). Exemplary gelling agents include, but are not limited to, carbomer, carboxyethylene or polyacrylic acid such as carbomer 980 or 940 NF, 981 or 941 NF, 1382 or 1342 NF, 5984 or 934 NF, ETD 2020, 2050, 934P NF, 971P NF, 974P NF, polycarbophils such as NOVEON AA-1, NOVEON CA1/CA2, carbomer copopolymers such as PEMULEN TR1 NF or PEMULEN TR2 NF, carbomer interpolymers such as CARBOPOL ETD 2020 NF, CARBOPOL ETD 2050 NF, CARBOPOL ULTRA EZ 10, etc . . . ; cellulose derivatives such as ethylcellulose, hydroxypropylmethylcellulose (HPMC), ethyl-hydroxyethylcellulose (EHEC), carboxymethylcellulose (CMC), hydroxypropylcellulose (HPC), hydroxyethylcellulose (HEC), etc . . . ; natural gums such as arabic, xanthan, guar gums, alginates, etc . . . ; polyvinylpyrrolidone derivatives; polyoxyethylene polyoxypropylene copolymers, etc; others like chitosan, polyvinyl alcohols, pectins, veegum grades, and the like. Other suitable gelling agents to apply the present invention include, but are not limited to, carbomers. Alternatively, other gelling agents or viscosant known by those skilled in the art may also be used. The gelling agent or thickener is present from about 0.2 to about 30% w/w depending on the type of polymer, as known by one skilled in the art. A preferred concentration range of the gelling agent(s), for example, hydroxypropyl cellulose or carbomer, is a concentration of between about 0.5 and about 5 weight percent, more preferred is a concentration of between about 1 and about 3 weight percent.

The gel formulations of the present invention may also further comprise a permeation enhancer (penetration enhancer). Permeation enhancers include, but are not limited to, sulfoxides such as dimethylsulfoxide and decylmethylsulfoxide; surfactants such as sodium laurate, sodium lauryl sulfate, cetyltrimethylammonium bromide, benzalkonium chloride, poloxamer (231, 182, 184), tween (20, 40, 60, 80) and lecithin; the 1-substituted azacycloheptan-2-ones, particularly 1-n-dodecylcyclazacycloheptan-2-one; fatty alcohols such as lauryl alcohol, myristyl alcohol, oleyl alcohol and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate, amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine, terpenes; alkanones, and organic acids, particularly salicylic acid and salicylates, citric acid and succinic acid. As noted earlier herein, "Percutaneous Penetration Enhancers", eds. Smith et al. (CRC Press, 1995), which is incorporated herein by reference thereto, provides an excellent overview of the field and further information concerning possible secondary enhancers for use in conjunction with the present invention. More permeation enhancer(s) suitable to be used with the present invention may be known by those skilled in the art. The permeation enhancer is present from about 0.1 to about 30% w/w depending on the type of compound. Preferred permeation enhancers are fatty alcohols and fatty acids. More preferred permeation enhancers are fatty alcohols. Preferably, the fatty alcohols have the formula the $CH_3(CH_2)n(CH)mCH_2OH$ wherein n ranges from (8–m) to (16–m) and m=0-2. A preferred concentration range of the penetration enhancer(s) is, depending on the type of permeation enhancer, a concentration of between about 0.1 and about 10 weight percent, as known by one skilled in the art. In one preferred embodiment, the penetration enhancer comprises myristyl alcohol in a concentration of between about 0.5 and about 2 weight percent.

A preferred concentration range of the antioxidant(s) of the gel formulations of the present invention, for example, tocopherol and derivatives, ascorbic acid and derivatives, butylated hydroxyanisole, butylated hydroxytoluene, fumaric acid, malic acid, propyl gallate, sodium metabisulfite and derivatives, is a concentration of about 0.01 to about 5 weight percent; more preferred is a concentration of about 0.1 to about 0.5 weight percent, depending on the type of antioxidant used, as known by the one skilled in the art.

A preferred concentration range of the buffering agent(s) of the gel formulations of the present invention, for example, carbonate buffers, citrate buffers, phosphate buffers, acetate buffers, hydrochloric acid, lactic acid, tartaric acid, inorganic and organic bases, is a concentration of about 1 to about 10 weight percent, more preferred is a concentration of about 2 to about 5 weight percent, depending on the type of buffering agent(s) used, as known by the one skilled in the art. Concentrations of the buffering agent(s) may vary, however, and the buffering agent may replace up to 100% of the water amount within the composition.

The transdermal or transmucosal pharmaceutical formulation of the present invention may also further include preservatives such as benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative is present from about 0.01 to about 10% w/w depending on the type of compound used, as known by the one skilled in the art.

The transdermal or transmucosal pharmaceutical formulation of the present invention may also further include humectants, sequestering agents, moisturizers, surfactants, emollients, colorants, fragrances, flavors, or any combination thereof.

In one embodiment, a gel formulation of the present invention comprises a therapeutically effective amount of nicotine, or a pharmaceutically acceptable salt thereof, of between about 0.5 to about 5 weight percent of nicotine free base equivalents. The primary vehicle may comprise between about 10 to about 60 weight percent of water, between about 30 to about 70 weight percent ethanol, between about 15 and about 60 weight percent of a 10:1 to 2:1 and 1:2 to 1:10 (weight to weight) mixture of diethylene glycol mono ethyl ether and propylene glycol, and between about 0.5 and about 2 weight percent of myristyl alcohol. The primary vehicle may be gellified with between about 0.5 and about 5 weight percent of hydroxypropyl cellulose. The apparent pH of the gel is between about pH 4.5 and about pH 8.5, or preferably between about pH 5.5 and pH 7.

Preferred embodiments of the present invention are gel formulations for non-occlusive therapeutic, transdermal applications. In such embodiments transdermal delivery methods or systems do not occlude the skin or mucosal surface from contact with the atmosphere by structural means, for example, there is no backing layer used to retain the gel formulation in place on skin or mucosal surface.

The formulations of the present invention may be provided in a unit dose container(s). Such containers typically comprise inner and outer surfaces, wherein the formulation of the present invention is contained by the inner surface of the container. In selected embodiments, the container is a packet or a vial, and the inner surface of the container may further comprise a liner. For example, in one embodiment, the container is a flexible, foil packet and the liner is a polyethylene liner. Alternatively, or in addition, the formulations of the present invention may be provided in a multiple dose container(s). Such multiple dose containers typically comprise inner and outer surfaces, wherein the gel for pharmaceutical drug delivery is contained by the inner surface of the container. Multiple dose containers may, for example, dispenses fixed or variable metered doses. Multiple dose containers may, for example, be a stored-energy metered dose pump or a manual metered dose pump.

In another aspect the present invention comprises a composition for pharmaceutical drug delivery, comprising a therapeutically effective amount of nicotine, or a pharmaceutically acceptable salt thereof, in a hydroalcoholic vehicle comprising water, a short chain alcohol, and at least one buffering agent. In such compositions the pH of the composition is typically between about pH 4.5 and about pH 8.5. Further, the transdermal flux (for example, instant flux) of the nicotine, in the hydroalcoholic vehicle, across skin is greater than the transdermal flux of an equal concentration of nicotine in an aqueous solution (that is, a solution without the short-chain alcohol solvent or other cosolvent) of essentially equivalent pH over an essentially equivalent time period, wherein the skin is the flux rate controlling membrane. These compositions for pharmaceutical delivery may include further components as described herein, for example, the hydroalcoholic vehicle may further comprise a permeation enhancer. Such compositions may be formulated in a variety of ways including wherein the hydroalcoholic vehicle is gellified. These compositions may be used, for example, for transdermal applications including application to skin and mucosal tissue (for example, intranasally, intrabucally, as a vaginal ovule or as a suppository).

In yet another aspect the present invention comprises a composition for pharmaceutical drug delivery, comprising a therapeutically effective amount of nicotine, or a pharmaceutically acceptable salt thereof, in a hydroalcoholic vehicle comprising water, a short chain alcohol, a monoalkyl ether of diethylene glycol, and a pharmaceutically acceptable glycol. In some embodiments, the nicotine is a pharmaceutically acceptable salt (for example, nicotine hydrogen tartrate). These compositions for pharmaceutical delivery may include further components as described herein, for example, the hydroalcoholic vehicle may further comprise a cosolvent(s), a penetration enhancer(s), a buffering agent(s), and/or a gelling agent(s). Such compositions may be formulated in a variety of ways including wherein the hydroalcoholic vehicle is gellified. These compositions may be used, for example, for transdermal applications including application to skin and mucosal tissue (for example, intranasally, intrabucally, as a vaginal ovule or as a suppository).

In a further aspect, the present invention includes methods of manufacturing the compositions described herein for pharmaceutical drug delivery. In one embodiment, the method of manufacturing comprises mixing the components to yield a homogeneous gel, wherein the pH of the gel is between about pH 4.5 and about pH 8.5 (exemplary components include, but are not limited to the following: a therapeutically effective amount of nicotine, or a pharmaceutically acceptable salt thereof; a primary vehicle comprising water, at least one short-chain alcohol, a monoalkyl ether of diethylene glycol, a pharmaceutically acceptable glycol, at least one gelling agent; and at least one buffering agent). These methods may include addition of further components as described herein, for example, the hydroalcoholic vehicle may further comprise an antioxidant(s), a cosolvent(s), a penetration enhancer(s), a buffering agent(s), and/or a gelling agent(s). The method provides a gel suitable for pharmaceutical delivery of nicotine. Further, a method of manufacturing may further include dispensing the pharmaceutical composition into one or more containers (for example, a unit dose container (e.g., a flexible, foil packet, further comprising a liner) or a multiple dose container).

In another aspect, the present invention includes methods for administering an active agent to a human subject in need thereof. For example, the method may comprise providing a composition of the present invention for transdermal, pharmaceutical delivery of nicotine. Doses of the compositions of the present invention may, for example, be a gel applied to the surface of skin. Further, doses of the compositions of the present invention may be applied in a single or in divided doses. In one embodiment, the composition is applied as one or more daily dose of the gel to a skin surface of the subject in an amount sufficient for the nicotine to achieve therapeutic concentration in the bloodstream of the subject. Nicotine, and pharmaceutical salts thereof, can be used for the treatment of a variety of conditions including smoking cessation, bowel irritable syndrome, neurological disorders, for example, anxiety, depression, schizophrenia, Alzheimer's Disease, Parkinson's Disease, Restless Legs Syndrome, Tourette's Syndrome, Chronic Tic Disorder, Essential Tremor, and Attention Deficit Hyperactivity Disorder. In one embodiment, the composition is a gel that has an amount of nicotine free base equivalents between about 0.5 and about 5 weight percent, wherein up to about 10 grams of the gel is applied daily to a skin surface area of between about 50 to about 1000 $cm^2$. In another embodiment, the composition is a gel that has an amount of nicotine free base equivalents of about 1.5 weight percent, wherein up to about 5 grams of the gel is applied daily to a skin surface area of between about 70 to about 800 $cm^2$.

In another aspect, the present invention includes dosage forms for delivery of nicotine that provide therapeutically effective steady-state plasma nicotine concentration to a subject. In one embodiment the steady-state plasma level is achieved by once-a-day dosing. With once-a-day dosing the maximum attained plasma concentration may be achieved more than about 24 hours after administration (that is, after administration of a second consecutive dose). The dosage form of the present invention is, in one embodiment, designed to be a once-a-day dosage form that provides continuous treatment of, for example, smoking cessation, irritable bowel syndrome, neurological disorders through delivery of therapeutically effective amounts of nicotine over 24 hours.

Embodiments of the present invention include a dosage form for delivery of nicotine to a subject comprising, a dose of nicotine, wherein said dosage form is configured to provide steady-state delivery of nicotine with once-a-day dosing. The once-a-day dosing is typically performed for at least about 2 consecutive days (that is, two days in succession) to achieve steady state plasma concentration of nicotine in the subject. In one embodiment, the dosage form comprises a dose of nicotine between about 0.5 to about 5 weight percent of nicotine free base equivalents, wherein dosage form is a pharmaceutical composition configured for transdermal administration (typically, non-occlusive, transdermal drug delivery).

The dosage forms of the present invention can be used, for example, for treatment of a disorder or condition (for example, a smoking cessation, irritable bowel syndrome, or a neurological disorder), as well as for use in preparation of a medicament to treat a disorder or condition.

The present invention provides, in one aspect, a controlled, sustained release of nicotine over a period of time sufficient to permit a once-a-day dosing. As described above, in one embodiment the dosage form is a composition configured for transdermal application. In other embodiments the dosage form may comprise, for example, nicotine formulations configured following the guidance of the specification in view of known formulation methods.

These and other objects of the invention will be apparent to one of ordinary skill in the art in view of the teachings presented herein. For example, the concentration of nicotine in the gel, the amount of gel applied daily, and the surface area over which the gel is applied may be varied by one of ordinary skill in the art in view of the teachings of the present application and the therapeutic needs of the subject being treated.

Figure 1B:
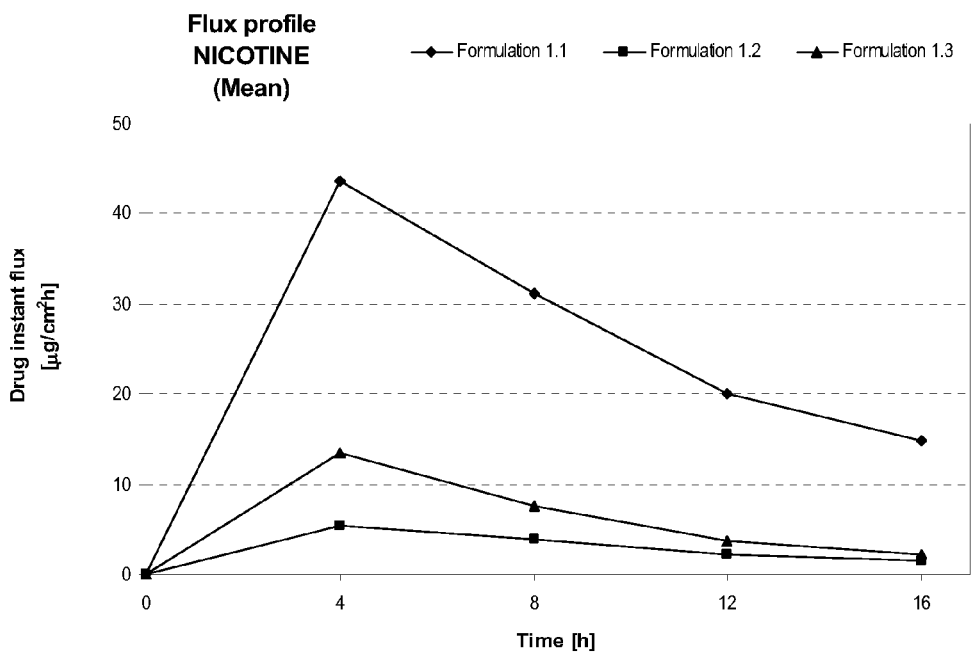
FIG. 1B shows data for flux results from the permeation analysis using the formulations in described in Example 1.

The active ingredient of the formulations of the present invention includes nicotine compounds and pharmaceutically acceptable salts thereof. A preferred nicotine compound is nicotine hydrogen tartrate. Traditionally, nicotine hydrogen tartrate has been delivered orally and nicotine free base has been delivered transdermally to patients in need of treatment (for example, HABITROL® (Novartis), NICODERM® CQ (Sanofi Aventis US), NICOTROL® (Pharmacia & Upjohn), PROSTEP® (AVEVA), etc . . . ). Nicotine patches were first introduced in the 1980s. In the late 90s, the nicotine transdermal systems became available as an OTC product to the public without a prescription. Initial experiments performed in support of the present invention demonstrated that non-occluded nicotine free base had good skin permeation characteristics (see, e.g., Example 1; FIGS. 1A and 1B). Nicotine formulations described herein provided sufficient transdermal flux for transdermal gel compositions to be used for therapeutic delivery of nicotine. In the initial study, a pharmaceutically acceptable salt of nicotine designed for oral delivery of nicotine (nicotine hydrogen tartrate) did demonstrate excellent skin permeation characteristics, very similar to skin permeation characteristic of nicotine free base designed for occlusive transdermal delivery of nicotine, while presenting several advantages over nicotine free base form: no unpleasant odor of tobacco, better chemical stability, better physical stability (color), and better appropriateness for sustained delivery.

In some embodiments, nicotine was formulated in a hydroalcoholic vehicle. Components of such hydroalcoholic vehicles include, but are not limited to, short-chain alcohols (for example, ethanol, propanol, isopropanol, butanol and/or mixtures of thereof) and water. Typically the short-chain alcohol(s) and water are considered the primary solvents. Further pharmaceutically acceptable solvents may be included in the formulations as well. In addition, the hydroalcoholic vehicle may include cosolvents, for example, non-volatile cosolvents. Examples of non-volatile solvents include, but are not limited to, propylene glycol, glycerin, liquid polyethylene glycols, polyoxyalkylene glycols, and/or mixtures thereof.

Experiments performed in support of the present invention provided the unexpected result that transdermal permeation of a pharmaceutically acceptable salt of nicotine (e.g., nicotine hydrogen tartrate) was sensitive to the concentration of the nicotine salt in the formulation, when the formulations are at the same pH (see, e.g., Example 5, FIGS. 5A and 5B). The cumulative transdermal permeation of nicotine in a lower concentration formulation of nicotine hydrogen tartrate (i.e., 2.85%, or 1% FBE) was approximately 75% of the transdermal permeation of nicotine with the higher concentration formulation of nicotine hydrogen tartrate (i.e., 5.7%, or 2% FBE). One advantage of obtaining a higher percentage transdermal permeation with pharmaceutically acceptable salts of nicotine (for example, nicotine hydrogen tartrate) is the ability to make stable pharmaceutically efficacious gel formulations using lower concentrations of nicotine while maintaining the ability to achieve the necessary steady state concentration of nicotine in the blood of a subject being treated with such gel formulations. Further, the differences in permeation illustrated by the experiments described herein allows flexibility in preparing formulations of nicotine and pharmaceutically acceptable salts thereof in order to achieve specific, therapeutic, steady-state target ranges for plasma concentrations of nicotine, for example, by choosing formulation concentrations of nicotine in the free base form, a pharmaceutically acceptable salt form such as the hydrogen tartrate form, or mixtures thereof.

Experiments performed in support of the present invention demonstrated the unexpected finding that the hydroalcoholic vehicle causes similar efficacious transdermal delivery of nicotine hydrogen tartrate over a wide range of pH from about pH 4.5 to about pH 8.5 (see, e.g., Example 2, FIGS. 2A and 2B; Example 3, FIGS. 3A and 3B; Example 4, FIGS. 4A and 4B), although absorption of nicotine hydrogen tartrate from gums by the oral mucosa is highly pH dependent (Clinical pharmacokinetics of nicotine, Svensson C K, Clin Pharmacokinet. 1987 January; 12(1):30-40.).

This provides an advantage for formulations of the present invention in that it helps facilitate adjustment of the pH of formulations to pH values closer to the physiological pH of human skin. Another advantage is that the efficacious transdermal delivery of nicotine hydrogen tartrate at the normal pH range of skin may help reduce the possibility of nicotine-dependent skin irritation that may be caused by transdermal administration of the formulations of the present invention. Further, the observed efficacious transdermal delivery of nicotine hydrogen tartrate may help reduce the amount of buffering agent that is added to formulations of nicotine useful for transdermal applications.

Accordingly the buffering agent (or buffering system) should be able to maintain the pH of the formulation in the target range (that is in the range of about pH 4.5 to about pH 8.5). After the addition of some buffering agents, further adjustment of pH may be desirable by addition of a second agent to achieve pH values in the target range. In view of the fact that the compositions of the present invention are directed to pharmaceutical use, the buffering agent or system should not be substantially irritating to skin or mucosal tissue to which the composition is being applied. Buffering agents include organic and non-organic buffering agents. Exemplary inorganic buffering agents include, but are not limited to, phosphate buffer solutions, carbonate buffers, citrate buffers, phosphate buffers, acetate buffers, sodium hydroxide, hydrochloric acid. Exemplary organic buffering agents include, but are not limited to, lactic acid, tartaric acid, meglumine, monoethanolamine, diethylamine, triethylamine, diisopropylamine, aminomethylamine, trihydroxymethylaminomethane, tetrahydroxypropylethylenediamine. Ultimately buffering agents are used at a concentration to achieve the desired target pH range; accordingly weight percent amounts of buffering agents may vary as may be determined by one of ordinary skill in the art in view of the teachings of the present specification. Buffering agents or systems in solution can, for example, replace up to 100% of the water amount within a given formulation. The concentration of a particular buffering agent (pH modifier) did not appear to have a significant effect on permeation and transdermal bioavailability of nicotine (see, e.g., Example 6, FIGS. 6A and 6B).

Hydroalcoholic vehicles of the present invention may be gellified, for example, by addition of a gelling agent. Suitable gelling agents of the present invention include, but are not limited to, carbomer, carbomer derivatives, carboxyethylene, polyacrylic acids (for example, Carbopol® (NOVEON Ip Holdings Corp. Cleveland, Ohio)), modified cellulose (for example, hydroxypropyl cellulose, hydroxyethyl cellulose, and carboxymethyl cellulose, ethylcellulose, hydroxypropylmethylcellulose, and ethylhydroxyethylcellulose,), polyvinyl alcohols, polyvinylpyrrolidone and derivatives, gums (for example, arabic, xanthan, guar gums, carragenans and alginates), and polyoxyethylene polyoxypropylene copolymers. Synonyms for carbopol include carbomer, poly(1-carboxyethylene) and poly(acrylic acid). In view of the teachings of the present specification, one having ordinary skill in the art may identify other gelling agents that are suitable in the practice of the present invention. The gelling agent may, for example, be present from about 1% to about 10% weight to weight of the composition. Preferably, the gelling agent is present from about 0.5% to about 5%, and more preferably, from about 1% to about 3% weight to weight of the composition.

The compositions of the present invention may further include a permeation enhancer(s). Permeation enhancers are well known in the art (see, for example, U.S. Pat. No. 5,807,570; U.S. Pat. No. 6,929,801; PCT International Publication No. WO 2005/039531; and "Percutaneous Penetration Enhancers", eds. Smith et al. (CRC Press, 1995)) and may be selected by one of ordinary skill in the art in view of the teachings presented herein for use in the compositions of the present invention. Permeation enhancers include, but are not limited to, sulfoxides, surfactants, fatty alcohols (for example, lauryl alcohol, myristyl alcohol, and oleyl alcohol), fatty acids (for example, lauric acid, oleic acid and valeric acid), fatty acid esters (for example, isopropyl myristate, isopropyl palmitate, methylpropionate, and ethyl oleate), polyols and esters thereof as well as mixtures (for example, propylene glycol, propylene glycol monolaurate), amides and nitrogenous compounds (for example, urea, dimethylacetamide, dimethylformamide, 2-pyrrolidone), and organic acids. The amount of permeation enhancer present in the composition will depend on a number of factors, for example, the strength of the permeation enhancer, the desired increase in skin permeability, the amount of drug to be delivered, the solubility of the drug in the matrix and the desired rate of administration. The effects of permeation enhancers in the compositions of the present invention can be evaluated by one of ordinary skill in the art following the teachings of the present specification (see, e.g., description of permeation study methods in the Materials and Methods section, herein below). Preferred ranges of permeation enhancer(s) in the compositions of the present invention are generally between about 0.1% and about 10% (w/w). Preferred permeation enhancers are fatty alcohols. More preferred permeation enhancer is myristyl alcohol.

Example 8 (Table 15) sets forth general formulation guidelines for some embodiments of gels for application to the skin surface of a subject in need of nicotine therapy. In these formulations, the primary vehicle of the transdermal gel formulations is a gellified hydroalcoholic mixture (e.g., ethanol/water/diethylene glycol mono ethyl ether/propylene glycol gellified with thickening agent). The transdermal gel formulations of the present invention contain a pharmaceutically effective amount of a nicotine compound (e.g., nicotine hydrogen tartrate), typically had a final pH of between about 4.5 and about 8.5, more preferably between about 5 and about 8, more preferably between about 5.5 and about 7.

Although preferred general components of the compositions of the present invention are described herein above, additional components may be included by one of ordinary skill in the art in view of the teachings presented herein. Further components may include, but are not limited to, humectants, moisturizers, surfactants, fragrances, flavors, preservatives, antioxidants, film-formers, and emollients. Preferred antioxidants are butyl hydroxyl toluene and sulfites. More preferred antioxidant is sodium metabisulfite.

In one aspect the present invention relates to a non occlusive gel formulation of nicotine that is able to deliver nicotine via transdermal application to a subject and achieve systemic absorption rates comparable or superior to transdermal occlusive systems of nicotine. In some embodiments, the present invention describes the use of a combination of permeation enhancers to achieve sustained transdermal delivery of nicotine. Typically the excipients and permeation enhancers used in the formulations of the present invention are either compendial or CFR listed; accordingly, no specific toxicity studies are required. The gel formulations of the present invention suitable for transdermal use represent an alternative to transdermal occlusive dosage forms and oral tablet dosing. Such formulations provide the advantages of delivering constant, sustained and smoothed plasmatic levels of nicotine while offering dose regimen flexibility and improved patient tolerance. Further, the gel formulations of the present invention provide an alternative route of administration for nicotine for subjects in need thereof, for example, geriatric patients who are often poly-medicated and sometimes have difficulty swallowing oral dosage forms. The gel formulations of the present invention can be provided for use in unit-dose packaging (for example, airless metered-dose pumps or single use pouches) to ease administration and ensure correct dosing for subjects.

Further, although preferred methods of administration are described herein (for example, gel compositions for application to skin surface), the compositions of the present invention are broadly suitable for use in transmucosal applications (for example, intranasal delivery, intrabuccal delivery, delivery by vaginal ovule or delivery by suppository) as can be determined by one of ordinary skill in the art in view of the teachings presented herein.

As described above, the present invention provides a dosage form comprised of a desired dose of nicotine, where the dosage form provides sustained release of nicotine. In general, the dosage form provides for the delivery of nicotine over a prolonged period of time such that once-a-day administration of the drug is possible. The dosage form may also deliver nicotine in a manner that results in relatively fewer and/or reduced side affects (for example, gastrointestinal side effects).

In addition to the nicotine dosage forms for transdermal application of the present invention, further dosage forms may be formulated following the guidance of the present invention in view of general teachings in the prior art related to the preparation of controlled release formulations of pharmaceutical agents (see, for example U.S. Pat. Nos. 5,156,850, 6,485,746, 6,770,297, 6,861,072, 6,946,146, 6,974,591, 6,987,082, 6,994,871, 7,008,641, and 7,022,339, Handbook of Pharmaceutical Excipients (Eds, R. C. Rowe, P. J. Sheskey and P. J. Weiler, Fourth Edition, American Pharmaceutical Association, The Pharmaceutical Press, London, 2003) Remington's Pharmaceutical Sciences (Arthur Osol, ed., pages 1553-1593 (1980))).

From the foregoing, it is apparent that the invention provides a non-occlusive dosage form with a profile that permits once daily dosing of nicotine which is similar to marketed transdermal nicotine patches.

Further, although preferred dosage forms are described herein, further dosage forms of the compositions of the present invention can be determined by one of ordinary skill in the art in view of the teachings presented herein.

Exemplary methods of making or manufacturing the compositions of the present invention are described herein below in the Materials and Methods section. Variations on the methods of making the compositions of the present invention will be clear to one of ordinary skill in the art in view of the teachings contained herein.

The manufacturing process for gel formulations of the present invention is straightforward and is typically carried out in a closed container with appropriate mixing equipment. For example, ethanol, propylene glycol, diethylene glycol mono ethyl ether are mixed in a primary container (reaction vessel) under a slight vacuum and nitrogen blanketing until a clear solution forms. In parallel, nicotine hydrogen tartrate is dissolved in a portion of water in a separate container and then added to the primary solution to prepare a hydro-alcoholic solution. The pH is then brought to its final value (e.g., approximately pH 6) by adding a fixed amount of buffering agent. The solution is gellified by addition of hydroxypropylcellulose and is then stirred until the hydroxypropylcellulose is completely swollen.

The compositions of the present invention may be applied to a skin surface or mucosal membrane using a variety of means, including, but not limited to a pump-pack, a brush, a swab, a finger, a hand, or other applicator.

The methods of manufacturing of the present invention may include dispensing compositions of the present invention into appropriate containers. The compositions of the present invention may be packaged, for example, in unit dose or multi-dose containers. The container typically defines an inner surface that contains the composition. Any suitable container may be used. The inner surface of the container may further comprise a liner or be treated to protect the container surface and/or to protect the composition from adverse affects that may arise from the composition being in contact with the inner surface of the container. Exemplary liners or coating materials include, but are not limited to high density polyethylene, low density polyethylene, very low density polyethylene, polyethylene copolymers, thermoplastic elastomers, silicon elastomers, polyurethane, polypropylene, polyethylene terephthalate, nylon, flexible polyvinylchloride, natural rubber, synthetic rubber, and combinations thereof. Liners or coating material are typically substantially impermeable to the composition and typically to the individual components of the composition.

A number of types of containers are known in the art, for example, packets with rupturable barriers (see, for example, U.S. Pat. Nos. 3,913,789, 4,759,472, 4,872,556, 4,890,744, 5,131,760, and 6,379,069), single-use packets (see, for example, U.S. Pat. Nos. 6,228,375, and 6,360,916), tortuous path seals (see, for example, U.S. Pat. Nos. 2,707,581, 4,491, 245, 5,018,646, and 5,839,609), and various sealing valves (see, for example, U.S. Pat. Nos. 3,184,121, 3,278,085, 3,635, 376, 4,328,912, 5,529,224, and 6,244,468). One example of a unit dose container is a flexible, foil packet with a polyethylene liner.

Containers/delivery systems for the compositions of the present invention may also include a multi-dose container providing, for example a fixed or variable metered dose application. Multi-dose containers include, but are not limited to, a metered dose aerosol, a stored-energy metered dose pump, or a manual metered dose pump. In preferred embodiments, the container/delivery system is used to deliver metered doses of the compositions of the present invention for application to the skin of a subject. Metered dose containers may comprise, for example, an actuator nozzle that accurately controls the amount and/or uniformity of the dose applied. The delivery system may be propelled by, for example, a pump pack or by use of propellants (e.g., hydrocarbons, hydro fluorocarbons, nitrogen, nitrous oxide, or carbon dioxide). Preferred propellants include those of the hydrofluorocarbon (e.g., hydrofluoroalkanes) family, which are considered more environmentally friendly than the chlorofluorocarbons. Exemplary hydrofluoroalkanes include, but are not limited to 1,1,1,2-tetrafluoroethane (HFC-134(a)), 1,1,1,2,3,3,3,-heptafluoropropane (HFC-227), difluoromethane (HFC-32), 1,1,1-trifluoroethane (HFC-143(a)), 1,1,2,2-tetrafluoroethane (HFC-134), 1,1-difluoroethane (HFC-152a), as well as combinations thereof. Particularly preferred are 1,1,1,2-tetrafluoroethane (HFC-134(a)), 1,1,1,2,3,3,3,-heptafluoropropane (HFC-227), and combinations thereof. Many pharmaceutically acceptable propellants have been previously described and may be used in the practice of the present invention in view of the teachings presented herein. The delivery system should provide dose uniformity. In a preferred embodiment, airless packaging with excellent barrier properties is used to prevent oxidation of nicotine, for example, airless metered-dose pumps wherein the composition comprising nicotine is packaged in collapsible aluminum foils. Accurate dosing from such pumps ensures reproducibility of dose.

The present invention further includes methods for administering a composition of the present invention to a subject in need thereof. Compositions of the present invention comprising nicotine can be employed, for example, for the treatment of a variety of conditions and/or disease states which have been historically treated by oral doses or transdermal occlusive doses of nicotine (for example, using HABITROL®). Nicotine therapy has been used to treat a variety of diseases and disorders of the central nervous system. Some specific conditions/disease states responsive to treatment with nicotine include, but are not limited to, anxiety, depression, schizophrenia, Alzheimer's Disease, Parkinson's Disease, Restless Legs Syndrome, Tourette's Syndrome, Chronic Tic Disorder, Essential Tremor, and Attention Deficit Hyperactivity Disorder, irritable bowel syndrome.

The nicotine compositions of the present invention may be self-applied by a subject in need of treatment or the composition may be applied by a care-giver or health care professional. The compositions may be applied in single daily doses, multiple daily doses, or divided doses. Transdermal delivery of nicotine, as described herein, provides a number of advantages relative to oral dosing, including, but not limited to, continuous delivery which provides for steady-state blood levels of the nicotine, avoidance of the first-pass effect, and substantial avoidance of gastrointestinal and many other side effects. The likelihood of patient acceptance may also be much improved particularly among populations that have difficulty swallowing or chewing, for example, some elderly subjects and pediatrics. In view of the aforementioned, skin irritation arising from use of the non-occlusive compositions of the present invention is likely to be non-existent or minimal; however, evaluation of the degree of skin irritation caused by the nicotine formulations of the present invention may be tested in standard animal models.

Ease of application of the non-occlusive compositions of the present invention, for example, gel formulations comprising nicotine hydrogen tartrate, provides several advantages relative to oral administration of nicotine. For example, when the subject in need of treatment cannot self-medicate (e.g., young children or the infirmed) transdermal delivery avoids forcing subjects to take and swallow a pill or chew a gum. Further, transdermal application of the non occlusive compositions of the present invention assures correct dosing, versus a pill that may be inappropriately chewed (for example, when the pill is a time-release formulation), spit out, and/or regurgitated. Dose escalation or titration is particularly facilitated by a nicotine non occlusive transdermal gel in that larger doses may be administered by increasing the area of application to the skin while keeping the concentration of the formulation fixed.

In one embodiment of the present invention, up to about 5 grams of a gel formulation, having an amount of nicotine free base equivalents between about 0.5 and about 5 weight percent, is applied daily to a skin surface area of between about 50 to about 1000 $cm^2$. In another embodiment, up to about 5 grams of a gel formulation, having an amount of nicotine free base equivalents of about 1.5 weight percent, is applied daily to a skin surface area of between about 70 to about 1000 $cm^2$.

In one embodiment of the present invention, experiments performed in support of the present invention have provided good in vitro/in vivo correlation based on bioavailability of nicotine in the compositions of the present invention. These results are intended for illustration purposes only and to provide a general basis for in vitro/in vivo comparison, thus they should not be considered limiting. As a first example, in vitro/in vivo correlation based on bioavailability of formulations presented in the Examples hereinafter may be evaluated as follows. In vitro data can be extrapolated to in vivo conditions in order to evaluate the gel dose for bioequivalence to occlusive nicotine transdermal absorption. NICORETTE® patches are transdermal delivery systems for topical application of nicotine base, available in sizes of 30, 20 and 10 cm2 each containing 0.83 $mg/cm^2$ of nicotine, releasing 15 mg, 10 mg and 5 mg respectively over 16 hours (see, for example, NICORETTE® Prescribing Information, GlaxoSmithKline, Middlesex UK). Considering the difference of transdermal in vitro bioavailability of formulation 7.2 in comparison with the intermediate dose of the 10 mg/16 hours NICORETTE® patch, formulation 7.2 would be bioequivalent to the 10 mg/16 hours NICORETTE® patch if about 3.7 g of the formulation 7.2 gel is applied over about 660 $cm^2$ of skin surface, for an intermediate gel loading of 5.6 $mg/cm^2$. This corresponds to a daily dose of 170 mg nicotine hydrogen tartrate (equivalent to about 60 mg free base).

Theoretical evaluations of transdermal nicotine delivery using exemplary compositions of the present invention have shown the feasibility to achieve therapeutic levels, for example, application of 0.5-10 g of gel at 4.6% nicotine hydrogen tartrate (equivalent to 1.5% nicotine free base) over 50-1000 $cm^2$ skin surface theoretically provides similar plasma levels as occlusive transdermal dose of NICORETTE® patches.

Because theoretical predictions of gel amount and skin application area from in vitro data may be underestimated or overestimated, the formulations of the present invention may be tested in a clinical setting for determination of actual dosing requirements for selected formulations of the present invention. Exact dosing requirements may be determined by one of ordinary skill in the art, for example, a research physician, in view of the teachings of the present specification. Further, such clinical testing provides information concerning therapeutic effectiveness of the nicotine formulations of the present invention for the treatment of a variety of conditions/disease states, as well as information regarding side-effects.

The following examples are illustrative of embodiments of the present invention and should not be interpreted as limiting the scope of the invention.

Experimental

The following examples are put forth so as to provide those of ordinary skill in the art with a complete disclosure and description of how to make and use the formulations, methods, and devices of the present invention, and are not intended to limit the scope of what the inventors regard as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The compositions produced according to the present invention meet the strict specifications for content and purity required of pharmaceutical products.

Materials and Methods

A. Pharmaceuticals and Reagents.

The pharmaceuticals and reagents used in the following examples can be obtained from commercial sources, for example, as follows: active drug (e.g., nicotine free-base form and nicotine hydrogen tartrate, from Siegfried Ltd, Zofingen, Switzerland or from Sigma-Aldrich Corporation, St. Louis, Mo.); penetration enhancers (e.g., diethylene glycol mono ethyl ether, also called TRANSCUTOL®P, from Gattefosse Corporation, Paramus, N.J.; myristyl alcohol, from Sigma-Aldrich Corporation, St. Louis, Mo.); solvents and cosolvents (e.g., ethanol, propylene glycol, from Sigma-Aldrich Corporation, St. Louis, Mo.); antioxidants (e.g., butylhydroxytoluene (BHT), butylhydroxyanisole (BHA), sodium metabisulfite, from Sigma-Aldrich Corporation, St. Louis, Mo.); thickening or gelling agents (e.g., hydroxypropyl cellulose, from Sigma-Aldrich Corporation, St. Louis, Mo.; or KLUCEL® (Aqualon Company, Wilmington Del.) hydroxypropyl cellulose, from Hercules, Inc., Wilmington, Del.); and standard pharmaceutical and chemical reagents (e.g., triethanolamine, sodium hydroxide, from Sigma-Aldrich Corporation, St. Louis, Mo.).

B. In Vitro Skin Permeation Methodology.

The in vitro human cadaver skin model has proven to be a valuable tool for the study of percutaneous absorption and the determination of topically applied drugs. The model uses human cadaver skin mounted in specially designed diffusion cells that allow the skin to be maintained at a temperature and humidity that match typical in vivo conditions (Franz, T. J., "Percutaneous absorption: on the relevance of in vitro data," J. Invest Dermatol 64:190-195 (1975)). A finite dose (for example: 4-7 mg/cm$^2$) of formulation is applied to the outer surface of the skin and drug absorption is measured by monitoring its rate of appearance in the receptor solution bathing the inner surface of the skin. Data defining total absorption, rate of absorption, as well as skin content can be accurately determined in this model. The method has historic precedent for accurately predicting in vivo percutaneous absorption kinetics (Franz, T. J., "The finite dose technique as a valid in vitro model for the study of percutaneous absorption in man," In: Skin: Drug Application and Evaluation of Environmental Hazards, Current Problems in Dermatology, vol. 7, G. Simon, Z. Paster, M Klingberg, M. Kaye (Eds), Basel, Switzerland, S. Karger, pages 58-68 (1978)).

Pig skin has been found to have similar morphological and functional characteristics as human skin (Simon, G. A., et al., "The pig as an experimental animal model of percutaneous permeation in man," Skin Pharmacol. Appl. Skin Physiol. 13(5):229-34 (2000)), as well as close permeability character to human skin (Andega, S., et al., "Comparison of the effect of fatty alcohols on the permeation of melatonin between porcine and human skin," J. Control Release 77(1-2):17-25 (2001); Singh, S., et al., "In vitro permeability and binding of hydrocarbons in pig ear and human abdominal skin," Drug Chem. Toxicol. 25(1):83-92 (2002); Schmook, F. P., et al., "Comparison of human skin or epidermis models with human and animal skin in in vitro percutaneous absorption," Int. J. Pharm. 215(1-2):51-6 (2001)). Accordingly, pig skin may be used for preliminary development studies and human skin used for final permeation studies. Pig skin can be prepared essentially as described below for human skin.

(i) Skin Preparation.

Percutaneous absorption was measured using the in vitro cadaver skin finite dose technique. Cryo-preserved, human cadaver trunk skin was obtained from a skin bank and stored in water-impermeable plastic bags at <−70° C. until used.

Prior to the experiment, skin was removed from the bag, placed in water (approximately 37° C.) for five minutes, and then cut into sections large enough to fit on 1 cm$^2$ Franz Cells (Crown Glass Co., Somerville, N.J.). Briefly, skin samples were prepared as follows. A small volume of phosphate buffered saline (PBS) was used to cover the bottom of the Petri dishes. Skin disks generally depleted of fat layers were placed in the Petri dishes for hydration. A Stadie-Riggs manual tissue microtome was used for slicing excised skin samples. Approximately 2 mL of PBS was placed into the middle cavity of the microtome as slicing lubricant. Skin disks were placed, dermal side up, into the middle cavity of the microtome. Filter paper was soaked with PBS, inserted in the cavity just above the skin disk. The filter paper prevented the dermis from sliding onto the top of the cutting block and helped to insure more precise cutting. When all three blades of the microtome were assembled, the microtome was turned into the upright position. Using a regular and careful sawing motion the skin tissue was sliced in cross-section. The skin tissue slice was removed with the tweezers and placed in the Petri dish for hydration. Each skin slice was wrapped in PARAFILM® (Pechiney Plastic Packaging, Inc., Chicago, Ill.) laboratory film and placed in water-impermeable plastic bags. Skin samples were identified by the donor and the provider code. If further storage was necessary, the skin slices were stored in the freezer at −20° C. until further use.

The epidermal cell (chimney) was left open to ambient laboratory conditions. The dermal cell was filled with receptor solution. Receptor solution for in vitro skin permeations was typically an isotonic saline at physiological pH. The receptor solution may also contain a drug solubilizer, for example, to increase lipophilic drug solubility in the receptor phase. The receptor solution was typically a phosphate buffered saline at approximately pH 7.4 (PBS, pH 7.4; European Pharmacopeia, 3rd Edition, Suppl. 1999, p. 192, No. 4005000) with addition of 2% Volpo N20 (oleyl ether of polyethylene glycol, a nonionic surfactant with HLB 15.5 obtained by ethoxylation (20 moles) of oleyl alcohol (C18:1)). This solubilizer is currently used for in vitro skin permeations and is known not to affect skin permeability (Bronaugh R. L., "Determination of percutaneous absorption by in vitro techniques," in: Bronaugh R. L., Maibach H. I. (Eds.), "Percutaneous absorption," Dekker, New York (1985); Brain K. R., Walters K. A., Watkinson A. C., Investigation of skin permeation in vitro, in: Roberts M. S., Walters K. A. (Eds.), Dermal absorption and toxicity assessment, Dekker, New York (1998)).

All cells were mounted in a diffusion apparatus in which the dermal bathing solution (i.e., the receptor solution) was stirred magnetically at approximately 600 RPM and skin surface temperature maintained at 33°±1° C.

Integrity of each skin section was determined before application of the test products by measurement of trans epidermal water loss (TEWL), using a TM 210 Tewameter (Courage-Khazaka, Germany). Differences between skin sections were determined statistically using unpaired p-test.

(ii) Dosing and Sample Collection.

(a) Franz Cell.

Just prior to dosing with the formulations described herein, the chimney was removed from the Franz Cell to allow full access to the epidermal surface of the skin. The formulations were typically applied to the skin section using a positive displacement pipette set to deliver approximately 6.25 mcL (6.25 mcL/1 cm$^2$). The dose was spread throughout the surface with the TEFLON® (E. I. Du Pont De Nemours And Company Corporation, Wilmington Del.) tip of the pipette. Five to ten minutes after application the chimney portion of the Franz Cell was replaced. Experiments were performed under non-occlusive conditions. Spare cells were not dosed, but sampled, to evaluate for interfering substances during the analytical analysis.

At pre-selected time intervals after test formulation application (e.g., 4, 8, 12, 16 hr) the receptor solution was removed in its entirety replaced with fresh solution (0.1× Phosphate Buffered Saline with Volpo (Croda, Inc., Parsippany, N.J.), and an aliquot taken for analysis. Prior to administration of the topical test formulations to the skin section, the receptor solution was replaced with a fresh solution of Volpo-PBS. (Volpo (Oleth-20) is a non-ionic surfactant known to increase the aqueous solubility of poorly water-soluble compounds. Volpo in the receptor solution insured diffusion sink conditions during percutaneous absorption, and is known not to affect the barrier properties of the test skin.)

Skin samples from three cadaver skin donors were prepared and mounted onto cells. Typically, each formulation was tested in 4 replicates (3 different donors).

Each formulation was applied, typically, to triplicate sections for each donor. The receptor solution samples were typically collected at 4, 8, 12, and 16 hours after dosing. The receptor solution used was phosphate buffered saline (PBS) at pH 7.4, with addition of 2% w/w Volpo N20 (oleyl ether of polyoxyethylene glycol). Differences between formulations were evaluated for statistical differences using standard statistical analysis, for example, the Student's t-Test. The samples were collected in 2 mL HPLC amber glass vials pre-sealed with septum crimp-caps and already containing 10 mcL of a solution of trifluoroacetic acid (TFA) 10%. Then they were transferred into Eppendorf microtubes, and centrifuged at 14500 RPM during 10 min. Each supernatant (0.9 mL) was transferred in a 2 mL HPLC amber glass vial. Analysis of the samples was performed by HPLC.

(b) Automatic Sampling

Automatic sampling was carried out essentially as described under "(a) Franz cell" above, with the exception that multiple cells were used coupled with an automatic sampling system. Skin from a single donor was cut into multiple smaller sections (e.g., punched skin disks cut to approximately 34 mm diameter) large enough to fit on 1 cm$^2$ Franz diffusion cells (Crown Glass Co., Somerville, N.J.).

Each dermal chamber was filled to capacity with a receptor solution (e.g., phosphate-buffered isotonic saline (PBS), pH 7.4±0.1, plus 2% Volpo), and the epidermal chamber was left open to ambient laboratory environment. The cells were then placed in a diffusion apparatus in which the dermal receptor solution was stirred magnetically at ~600 RPM and its temperature maintained to achieve a skin surface temperature of 32±1° C.

Typically, a single formulation was dosed to 2-3 chambers (comprising the same donor skin) at a target dose of about 5 uL/1 cm$^2$ using a calibrated positive displacement pipette. At pre-selected times after dosing, (e.g., 4, 8, 12, 16 h) the receptor solution was sampled and a predetermined volume aliquot saved for subsequent analysis. Sampling was performed using a Microette autosampler (Hanson Research, Chatsworth, Calif.).

Following the last receptor solution sample, the surface was washed and the skin collected for analysis as described herein.

(iii) Analytical Quantification Methods.

Quantification of Nicotine hydrogen tartrate was by High Performance Liquid Chromatography (HPLC) with Diode-Array and Mass spectrometry detector (HPLC/MS). Briefly, HPLC was conducted on a HEWLETT-PACKARD® (Hewlett-Packard Company, Palo Alto, Calif.) 1100 Series system with diode-array UV detector with MS detector. A solvent system consisting of 20%: (A) 0.5% $H_2O:H_3PO_4$ 100:1 adjusted to pH 3 with TEA and 80% (B) Methanol was run through a CN Spherisorb column (4.6×150 mm, 5 µl, Waters) at a flow rate of 1.4 mL/min (5-minute run duration). Twenty-five micro liters of sample were injected. Peak areas were quantified to concentration using an external standard curve prepared from the neat standard.

(iv) Data Analysis. The permeation studies described herein provide data to obtain different profiles of the transdermal absorption of nicotine through the skin as a function of time.

The absolute kinetic profile shows the mean cumulated nicotine permeated amount (e.g., µg/cm$^2$) as a function of time (e.g., hours) and thus provides an evaluation of the daily absorbed dose (amount of nicotine transdermally absorbed after 16 hours of permeation).

The relative kinetic profile shows the mean cumulated nicotine permeated amount (e.g., percent) as a function of time (e.g., hours) and thus allows an evaluation of the percentage of the applied nicotine that is transdermally absorbed after a given time.

The flux profile shows the mean nicotine instant flux [e.g., µg/cm$^2$/h] as a function of time (e.g., hours) and provides a time the steady-state flux is reached. This profile also provides an evaluation of the value of this steady-state flux. This value corresponds to the mean flux obtained at steady-state.

These different profiles provide means to evaluate, characterize, and compare formulations, as well as to assess the pharmaceutical efficacy of formulations and consequently, to optimize prototype formulations.

C. Formulation of Pharmaceutical Compositions.

Experiments performed in support of the present invention showed that the order of addition of the components was not significant, that is, the components may be added in essentially any order during manufacturing processes. Further, nitrogen sparging is not required during manufacturing of the pharmaceutical compositions of the present invention but use of nitrogen sparging is also not counter-indicated. In the pharmaceutical formulations described herein below, the solubility of the active ingredient (e.g., nicotine or nicotine hydrogen tartrate) was not an issue.

Following here is an exemplary description of the manufacturing process used to make the pharmaceutical compositions of the present invention. Generally, the organic solution was prepared, comprising, for example, solvent/cosolvent (e.g., ethanol/water/diethylene glycol mono ethyl ether/propylene glycol), penetration enhancer, and thickening (or gelling) agent. The organic solution was mixed (e.g., using mechanical mixing) to yield a homogeneous, clear solution. The active agent, nicotine, was then added to the solution and the solution mixed to obtain a homogeneous, clear active organic solution. Water was then added quantum sufficiat (q.s.). If desired, the pH was then adjusted to a specified pH. In some cases, water was added and pH was adjusted before the addition of nicotine so that nicotine was not exposed to high local pH variations; although timing of the pH adjustment was not an issue. Some compositions were purged of air by nitrogen bubbling before nicotine was dissolved; however, as noted above, such nitrogen sparging was not required. As noted above, the components may be added in essentially any order during manufacturing processes.

One exemplary method of manufacturing is as follows. Ethanol, propylene glycol, diethylene glycol mono ethyl ether (and myristyl alcohol) were weighed and added successively. The organic solution was mixed until homogenized using mechanical mixing (e.g., magnetic stirring). The resulting organic solution was clear and homogeneous. Nicotine hydrogen tartrate was added to 85-90% of the total amount of water and mixed until the solution was homogenized. Then the active aqueous solution was added to the organic solution and mixed until homogenization of the solution was achieved. The resulting solution was clear and homogeneous. Then triethanolamine (typically about 50% w/w aqueous solution) was added and the solution mixed until the solution was homogeneous. The resulting solution was clear and homogeneous with a pH, for example, of about 6. When the pH was within the desired specification range water was added q.s. to the solution to obtain final appropriate weight percents of components and the pH of the final solution measured. If the pH was below the desired pH (e.g., about pH 5.5), further triethanolamine solution was added and the pH of the final solution re-measured. Typically total triethanolamine amount did not exceed 5% w/w.

Example 1

Intrinsic In Vitro Permeation Results

Table 1 describes formulations that were evaluated for in vitro permeation. Evaluation of in vitro permeation was carried out as described in the Materials and Methods section using Franz cells.

TABLE 1

Composition of Formulations (% w/w)

| Formulation | Drug | Formulation (%) | Drug Concentration (%) |
|---|---|---|---|
| 1.1 | S(-) Nicotine Base | NICORETTE ® 10 mg/16 h TTS | 0.83 mg/cm$^2$ (20 cm$^2$) |
| 1.2 | S(-) Nicotine Base | Dow Corning ST Elastomer 10(74.25)/ Cyclomethicone 5NF(24.75) | 1.25 |
| 1.3 | S(-) Nicotine Base | Dow Corning ST Elastomer 10(73.5)/ Cyclomethicone 5NF(24.50) | 2.50 |

In Table 1, the formulation and drug concentration percentages are given in weight percent. For Formulations 1.2 and 1.3, the nicotine free base was simply admixed to the mixture of silicones. The primary purpose of using these formulations was to evaluate intrinsic permeation of nicotine free base from a non occlusive semi solid formulation and to compare it to skin permeation of nicotine free base from a marketed occlusive nicotine patch.

Pig ear skin was used for the permeation studies using Franz cells as described in the Materials and Methods.

The absolute kinetic profiles of the permeation analysis using the formulations in Table 1 are presented FIG. 1AB. In FIG. 1A, the vertical axis is Cumulated nicotine permeated (μg/cm$^2$), the horizontal axis corresponds to sampling times (in hours). The flux results of the permeation analysis using the formulations in Table 1 are presented FIG. 1B. In FIG. 1B, the vertical axis is Flux (μg/cm$^2$/hr), the horizontal axis corresponds to sampling times (in hours). Values for nicotine free base from reference NICORETTE® patch are represented using a diamond, flux values for nicotine free base from Formulation 1 are represented using a square, and flux values for nicotine free base from Formulation 1 are represented using an upright triangle.

The data presented in FIGS. 1A and 1B demonstrate that the amount of nicotine free base delivered from the 20 cm$^2$ NICORETTE® patch is 438.3 μg/cm$^2$ over 16 hours. Extrapolating to 20 cm$^2$, the patch system should deliver 20×0.4383=8.8 mg nicotine, to be compared with the in vivo data claimed by the label of the NICORETTE® patch (10 mg nicotine free base delivered over a period of 16 hours). Ratio in vivo/in vitro is therefore 1.14 which shows a good in vivo/in vitro correlation. Assuming that the same in vivo/in vitro ratio is observed with formulations 1.2 and 1.3, formulation 1.2 containing about 1.5% nicotine free base would deliver in vivo 51.84×1.14=59.1 μg/cm$^2$ and formulation 1.3 containing about 2.5% nicotine free base would deliver in vivo 108.23×1.14=123.5 μg/cm$^2$. Therefore, considering an average loading of about 5.6 mg of gel per square centimeter of skin, application of about 0.95 g of formulation 1.2 onto about 170 cm$^2$ skin surface, or application of about 0.45 g of formulation 1.3 onto about 80 cm$^2$ skin surface would deliver similar levels of nicotine free base than NICORETTE® 10 mg/16 h patch. Hence it is demonstrated that the nicotine free base demonstrated good permeation characteristics from a non occlusive transdermal dosage form.

These in vitro permeation results for the free base of nicotine demonstrated adequate intrinsic flux in an un-optimized formulation for use in pharmaceutical transdermal delivery of the drug.

These in vitro permeation results demonstrate that nicotine free base in a non occlusive gel can provide sufficient transdermal flux for transdermal gel compositions to be used for therapeutic delivery of nicotine.

However, it is well known from the art that nicotine free base is a labile compound that may easily evaporate and/or undergo oxidative degradation: see, for instance, Ikinci et al., in "Development and in vitro/in vivo evaluations of bioadhesive buccal tablets for nicotine replacement therapy", Pharmazie, Volume: 61, Issue: 3, Page(s): 203-207, March 2006.

Furthermore, nicotine free base is also handicapped by its strong odor of tobacco.

Nicotine salts in general, and nicotine hydrogen tartrate or nicotine bitartrate dihydrate in particular, do present significant advantages, both in regards of stability and odor, over nicotine free base. For illustration, loss of nicotine content (7.3%) from formulation 5.3—nicotine hydrogen tartrate 2% FBE—(see Example 5 herein after) was lower after 6 month storage at 40° C./25% R.H. than loss of nicotine content (7.4%) from formulation similar to formulation 1.2 described herein below after as little as one month storage at ambient temperature (typically 21° C.) under similar storage conditions (storage at dark in an airtight container).

As well-known in prior art, usually the free base form of a drug is preferred over a salt form when developing a transdermal drug product: see, e.g., scopolamine patch, fentanyl patch, clonidine patch. The free base forms generally have higher lipid solubility, lower melting point (the solubility of a compound is related to its melting point, and in generally compounds that have low melting points are good permeants), lower molecular weight than the more water-soluble salt forms (this is indeed verified for nicotine free base versus nicotine hydrogen tartrate). Therefore the free base form of a drug shows better permeation than its more water-soluble salt forms (see Hadgraft in Transdermal Delivery: Present and Future Perspectives", The Drug Delivery Reports Company Spring/Summer 2003, A) ©PharmaVentures Ltd 2003.

Indeed, nicotine salts (more particularly nicotine hydrogen tartrate and nicotine bitartrate dihydrate) are used traditionally in oral dosage forms such as pills, tablets and gums, as an alternative to complexes of nicotine free base with polacrilex resins, which are complex to manufacture and which present a higher cost of goods, while nicotine free base is traditionally used in transdermal drug products.

Surprisingly, despite their better chemical stability, their better physical stability (color), their lack of strong tobacco odor, nicotine tartrate salts are not used in any occlusive therapeutic transdermal systems currently marketed, and even less so in any marketed non occlusive therapeutic transdermal compositions

Example 1bis

Intrinsic In Vitro Permeation Results

Table 1bis herein below describes formulations that were evaluated for in vitro permeation. Evaluation of in vitro permeation was carried out as described in the Materials and Methods section using Franz cells.

TABLE 1bis

Composition of Formulations (% w/w)

| Formulation | Drug | Formulation (%) | Drug Concentration (%) |
|---|---|---|---|
| 1.1bis | S(−) Nicotine Base | NICORETTE® 10 mg/16 h TTS | 0.83 mg/cm² (20 cm²) |
| 1.2bis | S(−) Nicotine Base | Non occlusive hydro-or-ganic solution thickened with hydroxypropylcellulose cellulose and adjusted to pH close to 6.0 | 1.50 |
| 1.3bis | Nicotine Bitartrate Dihydrate | | 4.60* |

*Nicotine bitartrate 4.60% (MW = 498.2) corresponds to nicotine free base 1.5% (MW = 162.234), ratio 3.07.

In Table 1bis, the formulation and drug concentration percentages are given in weight percent. Drug carrier was similar in formulations 1.2bis and 1.3bis. The primary purpose of using these formulations was to evaluate permeability of the nicotine free base versus the permeability of a tartrate salt of nicotine from a non occlusive semi solid formulation and to compare it to skin permeation of nicotine free base from a marketed occlusive nicotine patch.

Pig ear skin was used for the permeation studies using Franz cells as described in the Materials and Methods.

The absolute kinetic profiles of the permeation analysis using the formulations in Table 1bis are presented FIG. 1Abis. In FIG. 1Abis, the vertical axis is Cumulated nicotine permeated ($\mu g/cm^2$), the horizontal axis corresponds to sampling times (in hours). The flux results of the permeation analysis using the formulations in Table 1bis are presented FIG. 1Bbis. In FIG. 1Bbis, the vertical axis is Flux ($\mu g/cm^2/hr$), the horizontal axis corresponds to sampling times (in hours). Values for nicotine free base from reference NICORETTE® patch are represented using a diamond, flux values for nicotine free base from Formulation 1 are represented using a square, and flux values for nicotine free base from Formulation 1 are represented using an upright triangle.

The data presented in FIGS. 1Abis and 1Bbis demonstrate that the amount of nicotine delivered from formulation 1.2bis after 16 hours (32.729 $\mu g/cm^2$) containing nicotine free base is very similar to the amount of nicotine delivered from formulation 1.3bis after 16 hours (31.092 $\mu g/cm^2$) containing the tartrate salt of nicotine.

The 20 cm² NICORETTE® 10 mg/16 hours patch is delivering 400.154 $\mu g/cm^2$ over 16 hours. Extrapolating to 20 cm², the patch system should deliver 20×0.4001=8 mg nicotine, to be compared with the in vivo data claimed by the label of the NICORETTE® patch (10 mg nicotine free base delivered over a period of 16 hours). Ratio in vivo/in vitro is therefore 1.25 which shows a good in vivo/in vitro correlation. Assuming that the same in vivo/in vitro ratio is observed with formulations 1.2bis and 1.3bis, formulation 1.2bis containing about 1.5% nicotine free base would deliver in vivo 32.73× 1.25=40.9 $\mu g/cm^2$ and formulation 1.3bis containing about 1.5% nicotine free equivalents of nicotine tartrate salt would deliver in vivo 31.09×1.25=38.9 $\mu g/cm^2$. Therefore considering an average loading of about 5.6 mg of gel per square centimeter of skin, application of about 1.4 g of formulation 1.2bis or formulation 1.3bis onto about 250 cm² skin surface would deliver similar levels of nicotine free base than 20 cm² NICORETTE® 10 mg/16 h patch. Hence it is demonstrated that the tartrate salt of nicotine demonstrated as good permeation characteristics as nicotine free base from a non occlusive transdermal dosage form.

These in vitro permeation results for the tartrate salt of nicotine demonstrated adequate intrinsic flux in a formulation for use in pharmaceutical transdermal delivery of the drug.

These in vitro permeation results demonstrate that the tartrate salt of nicotine in a non occlusive gel can provide sufficient transdermal flux for transdermal gel compositions to be used for therapeutic delivery of nicotine.

Example 2

Nicotine Hydrogen Tartrate Skin Permeation

Table 2 presents exemplary components of nicotine hydrogen tartrate gel formulations used in the following experiments.

TABLE 2

Composition of Formulations (% w/w)

| General Component | Specific Component | Formulation 2.1 | Formulation 2.2 | Formulation 2.3 |
|---|---|---|---|---|
| Active Drug | Nicotine hydrogen tartrate* | 4.27 | 4.27 | 4.27 |
| Solvent | Absolute Ethanol | 40.00 | 40.00 | 40.00 |
| Cosolvents | Diethylene glycol mono ethyl ether | 0.00 | 5.00 | 5.00 |
| | Propylene glycol | 0.00 | 15.00 | 15.00 |
| Penetration enhancer | Myristyl alcohol | 0.00 | 0.00 | 1.00 |
| Gelling agent | Hydroxypropyl cellulose (Klucel HF) | 1.50 | 1.50 | 1.50 |
| pH Modifier | Triethanolamine (50% w/w) | 7.43 | 7.10 | 7.19 |
| Solvent | Purified water | 46.80 | 27.13 | 26.04 |
| Final pH | | ~5.8 | ~5.8 | ~5.8 |
| Total | | 100.00 | 100.00 | 100.00 |

*Nicotine hydrogen tartrate 4.27% (MW = 462.401) corresponds to nicotine free base 1.5% (MW = 162.234), ratio 2.85.

Formulations 2.1, 2.2, and 2.3 were made essentially as described above in the Materials and Methods. Pig ear skin was used for the permeation studies using Franz cells as described in the Materials and Methods.

Transdermal delivery of nicotine hydrogen tartrate using Formulations 2.1, 2.2, and 2.3 was evaluated using an apparatus for automated sampling (described in the Materials and Methods Section). Individual gel amounts applied to tested skin samples were approximately 10 mg. Studies were performed according to OECD (Organization for Economic Cooperation and Development) guidelines (Organization for Economic Co-operation and Development (OECD), Environment Directorate. "Guidance document for the conduct of skin absorption studies," OECD series on testing and assessment, No. 28. Paris, version 5 Mar. 2004). The results presented in Table 3 show the mean values of cumulative delivered amount of nicotine after 16 hours. The total amount of nicotine in each of Formulations 2.1, 2.2, and 2.3 was the same.

TABLE 3

Nicotine Cumulative Delivery After 16 hours Permeation

| Formulation | N (number of samples) | Time (in hours) | Mean Cumulative Delivery ($\mu g/cm^2$) |
|---|---|---|---|
| 2.1 | 4 | 16 | 24.223 |
| 2.2 | 4 | 16 | 39.961 |
| 2.3 | 4 | 16 | 34.173 |

The absolute kinetic delivery profiles of nicotine over the 16 hour permeation are presented in FIG. 2A. In FIG. 2A, the vertical axis is Cumulated Drug Permeated ($\mu g/cm^2$), the horizontal axis is Time (in hours). Further, the transdermal flux profiles of nicotine over the 16 hour permeation are presented in FIG. 2B. In FIG. 2B, the vertical axis is Flux ($\mu g/cm^2/hr$), the horizontal axis corresponds to sampling times (in hours). The data points for Formulation 2.1 are presented as diamonds, the data points for Formulation 2.2 are presented as squares, the data points for Formulation 2.3 are presented as upright triangles.

The data presented in Table 3 and FIGS. 2A and 2B illustrate the surprising discovery that transdermal permeation of nicotine hydrogen tartrate is efficient from non-occlusive semi solid hydroalcoholic formulations in which it is contained at about pH 5.5-6.

Data from this study also demonstrate that transdermal nicotine hydrogen tartrate delivery can be outstandingly increased by further adding into the hydro-alcoholic semi solid non occlusive formulation cosolvents. Transdermal in vitro bioavailability was doubled (from about 27.7% to about 38.6%) in presence of diethylene glycol mono ethyl ether (5% w/w) combined with propylene glycol (15% w/w) (Formulation 2.1 versus Formulation 2.2). Further addition of permeation enhancer (for instance, myristyl alcohol) does not significantly either improve or impair nicotine hydrogen tartrate skin permeation: transdermal in vitro bioavailability is almost unchanged (from about 44.5% to about 38.6%) in presence of myristyl alcohol (1% w/w) (Formulation 2.2 versus Formulation 2.3). Therefore permeation enhancers in general and myristyl alcohol in particular, can be incorporated in the formulation of the present invention.

Formulations 2.1, 2.2 and 2.3 were also compared for nicotine crystallization kinetics. The objective was to establish a correlation between crystallization kinetics ("slow" or "fast" crystallization rate) of the formulations 2.1, 2.2 and 2.3 with absolute kinetic delivery profiles in vitro permeation and transdermal flux profiles of nicotine of these formulations.

An aliquot of the tested formulations 2.1, 2.2, and 2.3 was placed on a single glass plate, and then let at controlled room temperature (25° C.) and microscopy observations (×6.5 magnification, STEMI 2000-C microscope, Carl Zeiss, Germany) were made at different time points (5 minutes, 15 minutes, 45 minutes, and 90 minutes). After 5 minutes, formulation 2.1 presented massive polarization abnormalities all over the sample; formulation 2.2 presented minor polarization abnormalities; formulation 2.3 presented no polarization abnormalities. After 15 minutes, formulation 2.2 presented still minor polarization abnormalities; formulation 2.3 presented no polarization abnormalities. After 90 minutes, formulation 2.2 presented localized, moderate polarization abnormalities; formulation 2.3 still not presented polarization abnormalities.

Data from this microscopy study demonstrate that presence of cosolvents, namely the monoalkyl ether of diethylene glycol and the glycol, at such monoalkyl ether of diethylene glycol to glycol ratios (1:3 in the case of formulations 2.2 and 2.3), and at such combined amount of monoalkyl ether of diethylene glycol and glycol (20% by weight in the case of formulations 2.2 and 2.3) does delay (as in the case of formulation 2.2), or even prevent (as in the case of formulation 2.3) crystallization of active drugs.

Example 3

Further Investigation on Nicotine Hydrogen Tartrate Skin Permeation

Table 4 presents exemplary components of nicotine hydrogen tartrate gel formulations used in the following experiments.

TABLE 4

Composition of Formulations (% w/w)

| General Component | Specific Component | Formulation 3.1 | Formulation 3.2 | Formulation 3.3 |
|---|---|---|---|---|
| Active Drug | Nicotine hydrogen tartrate* | 2.85 | 2.85 | 2.85 |
| Solvent | Absolute Ethanol | 40.00 | 40.00 | 40.00 |
| Cosolvents | Diethylene glycol mono ethyl ether | 5.00 | 5.00 | 5.00 |
|  | Propylene glycol | 15.00 | 25.00 | 25.00 |
| Penetration enhancer | Myristyl alcohol | 1.00 | 1.00 | 0.00 |
| Gelling agent | Hydroxypropyl cellulose (Klucel HF) | 1.50 | 1.50 | 1.50 |
| pH Modifier | Triethanolamine (50% w/w) | 5.07 | 3.52 | 4.00 |
| Solvent | Purified water | 29.58 | 21.13 | 21.65 |
| Final pH |  | ~5.7 | ~5.4 | ~5.6 |
| Total |  | 100.00 | 100.00 | 100.00 |

*Nicotine hydrogen tartrate 2.85% (MW = 462.401) corresponds to nicotine free base 1% (MW = 162.234), ratio 2.85.

Formulations 3.1, 3.2, and 3.3 were made essentially as described above in the Materials and Methods. Pig ear skin was used for the permeation studies using Franz cells as described in the Materials and Methods.

Transdermal delivery of nicotine hydrogen tartrate using Formulations 3.1, 3.2, and 3.3 was evaluated using an apparatus for automated sampling (described in the Materials and Methods Section). Individual gel amounts applied to tested skin samples were approximately 10 mg. Studies were performed according to OECD (Organization for Economic Cooperation and Development) guidelines (Organization for Economic Co-operation and Development (OECD), Environment Directorate. "Guidance document for the conduct of skin absorption studies," OECD series on testing and assessment, No. 28. Paris, version 5 Mar. 2004). The results presented in Table 5 show the mean values of cumulative delivered amount of nicotine after 16 hours. The total amount of nicotine in each of Formulations 3.1, 3.2, and 3.3 was the same.

TABLE 5

Nicotine Cumulative Delivery After 16 hours Permeation

| Formulation | N (number of samples) | Time (in hours) | Mean Cumulative Delivery ($\mu g/cm^2$) |
|---|---|---|---|
| 3.1 | 4 | 16 | 23.886 |
| 3.2 | 4 | 16 | 16.428 |
| 3.3 | 4 | 16 | 10.945 |

The absolute kinetic delivery profiles of nicotine hydrogen tartrate over the 16 hour permeation are presented in FIG. 3A. In FIG. 3A, the vertical axis is Cumulated Drug Permeated (µg/cm²), the horizontal axis is Time (in hours). Further, the transdermal flux profiles of nicotine over the 16 hour permeation are presented in FIG. 3B. In FIG. 3B, the vertical axis is Flux (µg/cm²/hr), the horizontal axis corresponds to sampling times (in hours). The data points for Formulation 3.1 are presented as diamonds, the data points for Formulation 3.2 are presented as squares, the data points for Formulation 3.3 are presented as upright triangles.

The data presented in Table 5 and FIGS. 3A and 3B further illustrate the surprising discovery that transdermal permeation of nicotine hydrogen tartrate is efficient from non-occlusive semi solid hydroalcoholic formulations in which it is contained at about pH 5.5-6.

Data from this study also demonstrate that transdermal nicotine hydrogen tartrate delivery can be outstandingly modulated by varying the ratio of cosolvents present into the hydro-alcoholic semi solid non occlusive formulation. A huge decrease in transdermal in vitro bioavailability was observed (from about 39.6% to about 28.3%) when decreasing the ratio of diethylene glycol mono ethyl ether to propylene glycol from 1:3 to 1:5, the amount of the diethylene glycol mono ethyl ether being the same—5% w/w—(Formulation 3.1 versus Formulation 3.2).

Therefore transdermal in vitro bioavailability of nicotine hydrogen tartrate is unexpectedly proportional neither to the total amount of cosolvents nor to the ratio of cosolvents present in the hydro-alcoholic semi solid non occlusive formulation. Transdermal in vitro bioavailability of nicotine hydrogen tartrate rather follows a complex, non obvious pattern, with the existence of preferred optimal ratios of cosolvents (namely the diethylene glycol mono ethyl ether and the propylene glycol) and preferred total amount of cosolvents.

Data from this study further demonstrate that further addition of permeation enhancer(s) (for instance, myristyl alcohol) may increase nicotine hydrogen tartrate skin permeation: transdermal in vitro bioavailability is increased by about 50% (from about 19% to about 28.3%) in presence of myristyl alcohol (1% w/w) (Formulation 2.3 versus Formulation 2.2). Therefore permeation enhancers in general and myristyl alcohol in particular, can be incorporated in the formulation of the present invention.

Example 4

Further Investigation on Nicotine Hydrogen Tartrate Skin Permeation

Table 6 presents exemplary components of nicotine hydrogen tartrate gel formulations used in the following experiments.

TABLE 6

| General Component | Specific Component | Formulation 4.1 | Formulation 4.2 | Formulation 4.3 |
|---|---|---|---|---|
| Active Drug | Nicotine hydrogen tartrate* | 2.85 | 2.85 | 2.85 |
| Solvent | Absolute Ethanol | 40.00 | 40.00 | 40.00 |
| Cosolvents | Diethylene glycol mono ethyl ether | 5.00 | 5.00 | 2.50 |
|  | Propylene glycol | 15.00 | 10.00 | 15.00 |

TABLE 6-continued

| General Component | Specific Component | Formulation 4.1 | Formulation 4.2 | Formulation 4.3 |
|---|---|---|---|---|
| Penetration enhancer | Myristyl alcohol | 1.00 | 1.00 | 1.00 |
| Gelling agent | Hydroxypropyl cellulose (Klucel HF) | 1.50 | 1.50 | 1.50 |
| pH Modifier | Triethanolamine (50% w/w) | 4.23 | 4.84 | 4.32 |
| Solvent | Purified water | 30.42 | 34.81 | 32.83 |
| Final pH |  | ~5.6 | ~5.9 | ~5.8 |
| Total |  | 100.00 | 100.00 | 100.00 |

*Nicotine hydrogen tartrate 2.85% (MW = 462.401) corresponds to nicotine free base 1% (MW = 162.234), ratio 2.85.

Formulations 4.1, 4.2, and 4.3 were made essentially as described above in the Materials and Methods. Pig ear skin was used for the permeation studies using Franz cells as described in the Materials and Methods.

Transdermal delivery of nicotine hydrogen tartrate using Formulations 4.1, 4.2, and 4.3 was evaluated using an apparatus for automated sampling (described in the Materials and Methods Section). Individual gel amounts applied to tested skin samples were approximately 10 mg. Studies were performed according to OECD (Organization for Economic Cooperation and Development) guidelines (Organization for Economic Co-operation and Development (OECD), Environment Directorate. "Guidance document for the conduct of skin absorption studies," OECD series on testing and assessment, No. 28. Paris, version 5 Mar. 2004). The results presented in Table 7 show the mean values of cumulative delivered amount of nicotine after 16 hours. The total amount of nicotine in each of Formulations 4.1, 4.2, and 4.3 was the same.

TABLE 7

Nicotine Cumulative Delivery After 16 hours Permeation

| Formulation | N (number of samples) | Time (in hours) | Mean Cumulative Delivery (µg/cm²) |
|---|---|---|---|
| 4.1 | 4 | 16 | 24.852 |
| 4.2 | 3 | 16 | 18.120 |
| 4.3 | 3 | 16 | 18.490 |

The absolute kinetic delivery profiles of nicotine hydrogen tartrate over the 16 hour permeation are presented in FIG. 4A. In FIG. 4A, the vertical axis is Cumulated Drug Permeated (µg/cm²), the horizontal axis is Time (in hours). Further, the transdermal flux profiles of nicotine over the 16 hour permeation are presented in FIG. 4B. In FIG. 4B, the vertical axis is Flux (µg/cm²/hr), the horizontal axis corresponds to sampling times (in hours). The data points for Formulation 4.1 are presented as diamonds, the data points for Formulation 4.2 are presented as squares, and the data points for Formulation 4.3 are presented as upright triangles.

The data presented in Table 7 and FIGS. 4A and 4B further illustrate the surprising discovery that transdermal permeation of nicotine hydrogen tartrate is efficient from non-occlusive semi solid hydroalcoholic formulations in which it is contained at about pH 5.5-6.

Data from this study also further demonstrate that transdermal nicotine hydrogen tartrate delivery can be outstandingly modulated by varying the ratio of cosolvents present into the hydro-alcoholic semi solid non occlusive formulation. A huge decrease in transdermal in vitro bioavailability was observed (from about 43% to about 30.6%) when increasing the ratio of diethylene glycol mono ethyl ether to propylene glycol from 1:3 to 1:2, the amount of the diethylene glycol mono ethyl ether being the same—5% w/w—(Formulation 4.1 versus Formulation 4.2). Furthermore, a similar decrease in transdermal in vitro bioavailability was also observed (from about 43% to about 32.1%) when decreasing the ratio of diethylene glycol mono ethyl ether to propylene glycol from 1:3 to 1:5, the amount of the propylene glycol being the same—15% w/w—Formulation 4.1 versus Formulation 4.3).

Therefore data from this study further demonstrate that transdermal in vitro bioavailability of nicotine hydrogen tartrate is unexpectedly proportional neither to the total amount of cosolvents nor to the ratio of cosolvents present in the hydro-alcoholic semi solid non occlusive formulation. Transdermal in vitro bioavailability of nicotine hydrogen tartrate rather follows a complex, non obvious pattern, with the existence of preferred optimal ratios of cosolvents (namely the diethylene glycol mono ethyl ether and the propylene glycol) and preferred total amount of cosolvents.

Example 5

Drug Concentration Effects

Table 8 presents exemplary components of nicotine gel formulations used in the following experiments.

TABLE 8

Composition of Formulations (% w/w)

| General Component | Specific Component | Formulation 5.1 | Formulation 5.2 | Formulation 5.3 |
|---|---|---|---|---|
| Active Drug | Nicotine hydrogen tartrate* | 2.85 | 4.27 | 5.70 |
| Solvent | Absolute Ethanol | 40.00 | 40.00 | 40.00 |
| Cosolvents | Diethylene glycol mono ethyl ether | 5.00 | 5.00 | 5.00 |
|  | Propylene glycol | 15.00 | 15.00 | 15.00 |
| Penetration enhancer | Myristyl alcohol | 1.00 | 1.00 | 1.00 |
| Gelling agent | Hydroxypropyl cellulose (Klucel HF) | 1.50 | 1.50 | 1.50 |
| pH Modifier | Triethanolamine (50% w/w) | 5.07 | 7.19 | 8.52 |
| Solvent | Purified water | 29.58 | 26.04 | 23.28 |
| Final pH |  | ~5.7 | ~5.8 | ~5.7 |
| Total |  | 100.00 | 100.00 | 100.00 |

*Nicotine hydrogen tartrate 2.85% (MW = 462.401) corresponds to nicotine free base 1% (MW = 162.234), ratio 2.85.
*Nicotine hydrogen tartrate 4.27% (MW = 462.401) corresponds to nicotine free base 1.5% (MW = 162.234), ratio 2.85.
*Nicotine hydrogen tartrate 5.70% (MW = 462.401) corresponds to nicotine free base 2% (MW = 162.234), ratio 2.85.

Formulations 5.1, 5.2, and 5.3 were made essentially as described above in the Materials and Methods. Pig ear skin was used for the permeation studies using Franz cells as described in the Materials and Methods.

Transdermal delivery of nicotine using Formulations 5.1, 5.2, and 5.3 was evaluated using an apparatus for automated sampling (described in the Materials and Methods Section). Individual gel amounts applied to tested skin samples were approximately 10 mg. Studies were performed according to OECD (Organization for Economic Cooperation and Development) guidelines (Organization for Economic Co-operation and Development (OECD), Environment Directorate. "Guidance document for the conduct of skin absorption studies," OECD series on testing and assessment, No. 28. Paris, version 5 Mar. 2004). The results presented in Table 9 show the mean values of cumulative delivered amount of nicotine after 16 hours.

TABLE 9

Nicotine Cumulative Delivery After 16 hours Permeation

| Formulation | N (number of samples) | Time (in hours) | Mean Cumulative Delivery ($\mu g/cm^2$) |
|---|---|---|---|
| 5.1 | 4 | 16 | 13.651 |
| 5.2 | 4 | 16 | 20.700 |
| 5.3 | 4 | 16 | 24.006 |

The absolute kinetic delivery profiles of nicotine hydrogen tartrate over the 16 hour permeation are presented in FIG. 5A. In FIG. 5A, the vertical axis is Cumulated Drug Permeated ($\mu g/cm^2$), the horizontal axis is Time (in hours). Further, the transdermal flux profiles of nicotine over the 16 hour permeation are presented in FIG. 5B. In FIG. 5B, the vertical axis is Flux ($\mu g/cm^2/hr$), the horizontal axis corresponds to sampling times (in hours). The data points for Formulation 5.1 are presented as diamonds, the data points for Formulation 5.2 are presented as squares, and the data points for Formulation 5.3 are presented as upright triangles.

The data presented in Table 9 and FIGS. 5A and 5B illustrate the surprising discovery that transdermal permeation of nicotine hydrogen tartrate is sensitive to the concentration of the nicotine hydrogen tartrate in the formulation, when the formulations are at the same pH (e.g., pH 5.5-6). A strict dose/response curve would predict that the formulation of 2.85% nicotine hydrogen tartrate (i.e., 1% FBE) would have half of the cumulative transdermal permeation nicotine compared to the formulation of 5.70% nicotine hydrogen tartrate (i.e., 2% FBE). This was indeed the case: FIG. 5C shows a good correlation factor of 0.96.

In this example, the cumulative transdermal permeation of nicotine with the lower concentration formulation of nicotine hydrogen tartrate (i.e., 1% FBE) was approximately half (57% actually) of the transdermal permeation of nicotine with the higher concentration formulation of nicotine hydrogen tartrate (i.e., 2% FBE). However, transdermal permeation of nicotine with the intermediate concentration formulation of nicotine hydrogen tartrate (i.e., 1.5% FBE) was approximately 86% of the transdermal permeation of nicotine with the higher concentration formulation of nicotine hydrogen tartrate (i.e., 2% FBE), and about 152% the transdermal permeation of nicotine with the lower concentration formulation of nicotine hydrogen tartrate (i.e., 1% FBE). Therefore this intermediate concentration formulation of nicotine hydrogen tartrate (i.e., 1.5% FBE) represents the best balance between nicotine hydrogen tartrate applied dose and amount of nicotine transdermally absorbed.

Example 6

Nicotine Hydrogen Tartrate Skin Permeation pH Sensitivity

Table 10 presents exemplary components of nicotine gel formulations used in the following experiments. The effect of pH of formulations of the present invention on transdermal delivery of nicotine was assessed.

TABLE 10

Composition of Formulations (% w/w)

| General Component | Specific Component | Formulation 6.1 | Formulation 6.2 | Formulation 6.3 |
|---|---|---|---|---|
| Active Drug | Nicotine hydrogen tartrate* | 2.85 | 2.85 | 2.85 |
| Solvent | Absolute Ethanol | 40.00 | 40.00 | 40.00 |
| Cosolvents | Diethylene glycol mono ethyl ether | 5.00 | 5.00 | 5.00 |
| | Propylene glycol | 15.00 | 15.00 | 15.00 |
| Penetration enhancer | Myristyl alcohol | 1.00 | 1.00 | 1.00 |
| Gelling agent | Hydroxypropyl cellulose (Klucel HF) | 1.50 | 1.50 | 1.50 |
| pH Modifier | Triethanolamine (50% w/w) | 5.07 | 7.29 | 13.27 |
| Solvent | Purified water | 29.58 | 27.36 | 22.00 |
| Final pH | | ~5.7 | ~6.9 | ~7.9 |
| Total | | 100.00 | 100.00 | 100.00 |

*Nicotine hydrogen tartrate 2.85% (MW = 462.401) corresponds to nicotine free base 1% (MW = 162.234), ratio 2.85.

Formulations 6.1, 6.2, and 6.3 were made essentially as described above in the Materials and Methods. Pig ear skin was used for the permeation studies using Franz cells as described in the Materials and Methods.

Transdermal delivery of nicotine using Formulations 6.1, 6.2, and 6.3 was evaluated using an apparatus for automated sampling (described in the Materials and Methods Section). Individual gel amounts applied to tested skin samples were approximately 10 mg. Studies were performed according to OECD (Organization for Economic Cooperation and Development) guidelines (Organization for Economic Co-operation and Development (OECD), Environment Directorate. "Guidance document for the conduct of skin absorption studies," OECD series on testing and assessment, No. 28. Paris, version 5 Mar. 2004). The results presented in Table 11 show the mean values of cumulative delivered amount of nicotine after 16 hours.

TABLE 11

Nicotine Cumulative Delivery After 16 hours Permeation

| Formulation | N (number of samples) | Time (in hours) | Mean Cumulative Delivery ($\mu g/cm^2$) |
|---|---|---|---|
| 6.1 | 4 | 16 | 41.227 |
| 6.2 | 4 | 16 | 44.763 |
| 6.3 | 3 | 16 | 38.336 |

The absolute kinetic delivery profiles of nicotine hydrogen tartrate over the 16 hour permeation are presented in FIG. 6A. In FIG. 6A, the vertical axis is Cumulated Drug Permeated ($\mu g/cm^2$), the horizontal axis is Time (in hours). Further, the transdermal flux profiles of nicotine over the 16 hour permeation are presented in FIG. 6B. In FIG. 6B, the vertical axis is Flux ($\mu g/cm^2/hr$), the horizontal axis corresponds to sampling times (in hours). The data points for Formulation 6.1 are presented as diamonds, the data points for Formulation 6.2 are presented as squares, and the data points for Formulation 6.3 are presented as upright triangles.

Nicotine is an ionizable base, with pKa values of about 3.1 and 8.02 (Lide D R, ed. CRC Handbook of chemistry and physics. 71st ed. Boca Raton, Fla.: CRC Press, 1990.). The percentage of free (unprotonated) nicotine, which is dependent on the pH, can be determined according to the Henderson-Hasselbalch equation for weak base B:

$$[BH^+] = \frac{10^{pKa-pH}}{1 + 10^{pKa-pH}}$$

Absorption of nicotine depends on pH and the degree of ionization of this weak base, with the non-ionized form readily crossing the membrane. It is well known in the literature that alkaline pH facilitates absorption of nicotine through the mucosal surfaces and the skin (see S L Tomar and J E Henningfield, from the Office on Smoking and Health, US Centers for Disease Control and Prevention, Atlanta, Ga., USA in "Review of the evidence that pH is a determinant of nicotine dosage from oral use of smokeless tobacco", Tobacco Control, Vol 6, 219-225, 1997 by BMJ Publishing Group; Adrian C L, Olin H B, Dalhoff K, Jacobsen J, "In vivo human buccal permeability of nicotine", Int J Pharm. 2006 Mar. 27; 311(1-2):196-202. Epub 2006 Feb. 7.)

The data presented in Table 11 and FIGS. 6A and 6B illustrate the surprising discovery that the pH of the formulation had no significant effect on nicotine transdermal in vitro bioavailability. For example, pH increase from approximately pH 5.7 to 6.9 results in 6% increase of drug delivery. Even more strikingly, pH increase from approximately pH 5.7 to 7.9 results in 10% decrease in drug delivery. This is not consistent with teaching of the prior art. There is no need to increase pH of the formulations of the present invention in order to increase skin permeation of nicotine hydrogen tartrate.

The data support that a preferred range of final formulation pH for the transdermal delivery of nicotine is about pH 4.5 to about pH 8.5, with a more preferred range of final formulation pH of between about pH 5.5 to about pH 8, with an even more preferred range of final pH between about 5.5 to 7. For information, the pH of human skin is typically about pH 4.5-6.

One advantage of obtaining transdermal permeation of nicotine at pH values closer to the physiological pH of human skin than the pKa of free base nicotine (8) is a possible reduction in skin irritation potential at the site of application of transdermal formulations comprising nicotine thanks to the use of lower amounts of buffering agents, which are known to be irritant for the skin.

Another advantage of obtaining transdermal permeation of nicotine at pH values closer to the physiological pH of human skin than the pKa of free base nicotine (8) is a possible reduction in skin irritation potential at the site of application of transdermal formulations comprising nicotine thanks to the use of lower concentration of nicotine, which is known to elicit contact dermatitis when delivered transdermally (Bircher A J, Howald H, Rufli T., "Adverse skin reactions to nicotine in a transdermal therapeutic system", Contact Dermatitis. 1991 October; 25(4):230-6.). Noteworthy, skin irritation induced by nicotine is further emphasized by the use of patches as a way to deliver nicotine transdermally, because of the occlusive nature of the patches (preventing the skin from "breathing"), because of the very high nicotine loading per square centimeter, and because of the presence of the adhesive compounds. Therefore another obvious advantage of a formulation of nicotine hydrogen tartrate of the present invention is its non occlusive nature, thereby minimizing risks for skin irritation.

Another further advantage of obtaining a higher percentage transdermal permeation of nicotine hydrogen tartrate at pH values closer to the apparent pKa of nicotine in an alcohol/water solvent (i.e., apparent pKa 7.7) is the ability to make pharmaceutically efficacious gel formulations using lower concentrations of nicotine while maintaining the ability to achieve the necessary steady state concentration of nicotine in the blood of a subject being treated with such gel formulations.

Example 7

Nicotine Tartrate Salt Comparative Skin Permeation

Table 12 presents exemplary components of nicotine hydrogen tartrate gel formulations used in the following experiments.

TABLE 12

Composition of Formulations (% w/w)

| General Component | Specific Component | Formulation 7.1 | Formulation 7.2 | Formulation 7.3 |
|---|---|---|---|---|
| Active Drug | Nicotine bitartrate dihydrate* | 4.60 | 4.60 | NICORETTE ® 10 mg/16 hours |
| Solvent | Absolute Ethanol | 40.00 | 40.00 | |
| Cosolvents | Diethylene glycol mono ethyl ether | 5.00 | 5.00 | |
| | Propylene glycol | 15.00 | 15.00 | |
| Gelling agent | Hydroxypropyl cellulose (Klucel HF) | 1.50 | 1.50 | |
| pH Modifier | Triethanolamine | 3.55 | 3.55 | |
| Solvent | Purified water | 30.35 | 30.35 | |
| Final pH | | ~5.6 | ~5.6 | ~5.8 |
| Total | | 100.00 | 100.00 | 100.00 |

*Nicotine bitartrate dihydrate 4.627% (MW = 462.401) corresponds to nicotine free base 1.5% (MW = 162.234), ratio 2.85.

Formulations 7.1 and 7.3 were made essentially as described above in the Materials and Methods. Formulation 7.1 and 7.2 are identical, but formulation 7.1 was tested on pig ear skin, and formulation 7.2 was tested on frozen human abdominal skin. Formulation 7.3 (Reference marketed product) was also tested on frozen human abdominal skin. Permeation studies used Franz cells as described in the Materials and Methods. The aim of this study was to compare transdermal delivery of nicotine from non occlusive formulations of the present invention at nicotine tartrate salt 1.5% FBE on pig or human skin, and to compare it versus one reference marketed patch on human skin.

Transdermal delivery of nicotine hydrogen tartrate using Formulations 7.1, 7.2, and 7.3 was evaluated using an apparatus for automated sampling (described in the Materials and Methods Section). Individual gel amounts applied to tested skin samples were approximately 10 mg. Studies were performed according to OECD (Organization for Economic Cooperation and Development) guidelines (Organization for Economic Co-operation and Development (OECD), Environment Directorate. "Guidance document for the conduct of skin absorption studies," OECD series on testing and assessment, No. 28. Paris, version 5 Mar. 2004). The results presented in Table 13 show the mean values of cumulative delivered amount of nicotine after 16 hours. The total amount of nicotine in each of Formulations 7.1, 7.2, and 7.3 was the same.

TABLE 13

Nicotine Cumulative Delivery After 16 hours Permeation

| Formulation | N (number of samples) | Time (in hours) | Mean Cumulative Delivery ($\mu g/cm^2$) |
|---|---|---|---|
| 7.1 | 4 | 16 | 33.867 |
| 7.2 | 4 | 16 | 15.871 |
| 7.3 | 3 | 16 | 381.391 |

The absolute kinetic delivery profiles of nicotine over the 16 hour permeation are presented in FIG. 7A. In FIG. 7A, the vertical axis is Cumulated Drug Permeated ($\mu g/cm^2$), the horizontal axis is Time (in hours). Further, the transdermal flux profiles of nicotine over the 16 hour permeation are presented in FIG. 7B. In FIG. 7B, the vertical axis is Flux ($\mu g/cm^2/hr$), the horizontal axis corresponds to sampling times (in hours). The data points for Formulation 7.1 are presented as diamonds, the data points for Formulation 7.2 are presented as squares, the data points for Formulation 7.3 are presented as upright triangles.

The data presented in Table 13 and FIGS. 7A and 7B illustrate the surprising discovery that transdermal in vitro bioavailability of nicotine is affected by the type of skin membrane: transdermal in vitro bioavailability of nicotine is significantly decreased from 38% with fresh pig skin to 18% with frozen human skin (−52%, p=0.009). Compared to the in vivo clinical data (bioavailability of about 60%), transdermal in vitro bioavailability of the nicotine from the patch is 23% inferior to the transdermal in vivo bioavailability. This difference is commonly observed with patches (e.g. ORTHO-EVRA® patch) since effect of occlusion in vitro is not as effective as in vivo (blood microcirculation).

Based on data obtained on frozen human skin, and assuming the same in vivo/in vitro discrepancy is observed, bio similarity of the non occlusive formulation 7.2 of the present invention with marketed transdermal nicotine patches can be assessed (see table herein below):

TABLE 14

NICORETTE ® Patches Equivalencies

| Patch delivery rate | NICORETTE 5 mg/16 h | NICORETTE 10 mg/16 h | NICORETTE 15 mg/16 h |
|---|---|---|---|
| Eq. NIC applied dose [mg] | 27.8 | 55.6 | 83.3 |
| Eq. gel applied dose [g] | 1.85 | 3.7 | 5.6 |
| Eq. applied skin surface [$cm^2$]* | 330 | 660 | 990 |

*Calculations based on an average gel loading of about 5.6 g/$cm^2$

These doses of gel are totally in line with requirements of transdermal delivery route. For instance, ANDROGEL®, a gel formulation of testosterone indicated for hormonal replacement therapy in hypogonadal men, is being applied up to 10 grams a day.

Example 8

General Formulation Guidelines for Preferred Transdermal Gel Compositions

Based on experiments performed in support of the present invention, the following general formulation guidelines were determined for transdermal gel compositions comprising nicotine for pharmaceutical applications. Percentages given in Table 14 are approximate percentages. Variations on the compositions will be clear to one of ordinary skill in the art in view of the teachings of the present specification. Adjustment to volume to obtain total weight percent typically employs addition of alcohol, water, and/or cosolvent q.s.

TABLE 15

Composition of Formulations (% w/w)

| General Component | Preferred Range | More Preferred Range | Exemplary Component |
|---|---|---|---|
| Solvent: | | | |
| Alcohol | 30%-70% | 40%-60% | Absolute Ethanol |
| Water | 10%-60% | 15%-40% | Purified Water |
| Cosolvent: | | | |
| Glycol ether | 1%-30% | 2.5%-10% | Diethylene glycol mono ethyl ether (TC) |
| Glycol | 1%-30% | 10%-15% | Propylene glycol (PG) |
| Penetration enhancer | 0.1%-10% | 1%-2% | Myristyl alcohol |
| Gelling Agent | 0.5%-5% | 1%-3% | Hydroxypropyl cellulose |
| pH Modifier | 1%-10% | 3%-5% | Triethanolamine (50% w/w aqueous solution) |
| Active Drug | 0.5%-5% | 1%-2% | Nicotine hydrogen tartrate (free base equivalents*) |
| Final pH | 4.5-8.5 | 5.5-7.0 | |

*Nicotine hydrogen tartrate (MW = 462.401); nicotine free base (MW = 162.234), ratio 2.85.

The primary vehicle of the transdermal gel formulations of the present invention was a gellified hydroalcoholic mixture (e.g., ethanol/water gellified with hydroxypropyl cellulose). The transdermal gel formulations of the present invention contained a pharmaceutically effective amount of active drug (e.g., nicotine), typically had a final pH of between about 5.5 and 6.5, and, in some embodiments, further comprised permeation enhancer(s). In Table 12 the exemplary ranges are given as weight percents, with the exception of the final pH, wherein the range is presented as a target pH range.

The solvent is typically a mixture of solvents (solvent system), for example, alcohol, water, diethylene glycol monoalkyl ether and a glycol. Typically the ratio of the diethylene glycol mono alkyl ether to the glycol is 10:1 to 2:1, or 1:2 to 1:10. More preferred are ratios from 5:1 to 3:1 and from 1:3 to 1:5. Typically, the cumulated amount of the diethylene glycol mono alkyl ether and of the glycol is not less than 15% and not more than 60%. Typically the diethylene glycol mono alkyl ether is diethylene glycol mono ethyl, and the glycol is propylene glycol. The vapor pressure of the solvent system is typically such that the majority of the solvent is capable of evaporating at body temperature. The normal range of human body temperature is typically about 31-34° C., with an average of about 32° C. The gelling agent is typically present in an amount to impart a three-dimensional, cross-linked matrix to the solvent. The pH of the formulation is adjusted, for example, by addition of aqueous triethanolamine before the final volume of the formulation is brought to 100 g (basis for weight percent). Alternately or in addition, pH can be adjusted by titration and final total weight adjusted q.s., for example, with purified water.

Accordingly, in one embodiment of the present invention includes a formulation of nicotine in a hydroalcoholic gel, pH about 5.5 to about 7, which may further comprise antioxidant(s) and preservative(s).

As is apparent to one of skill in the art, various modification and variations of the above embodiments can be made without departing from the spirit and scope of this invention. Such modifications and variations are within the scope of this invention.

The numerous advantages of the present invention, comprising, but not limited to, the sustained transdermal delivery from a non occlusive formulation of a pharmaceutically acceptable salt of nicotine having no unpleasant odor of tobacco, having better chemical stability, having better physical stability (color), and having better appropriateness for sustained delivery of nicotine, are now set forth in the following claims.

What is claimed is:

1. A transdermal or transmucosal non occlusive pharmaceutical gel formulation comprising:
   a nicotine compound;
   a gelling agent; and
   a solvent system present in an amount sufficient to solubilize the nicotine and characterized in that it includes:
   (i) a pharmaceutically acceptable monoalkyl ether of diethylene glycol present in an amount of between about 1% and 30% by weight of the solvent system;
   (ii) a pharmaceutically acceptable glycol present in an amount of between about 1% and 30% by weight of the solvent system, with the monoalkyl ether of diethylene glycol and glycol being present in a weight ratio of 10:1 to 2:1 or 1:2 to 1:10; and wherein the monoalkyl ether of diethylene glycol and the glycol in combination are present in an amount of at least 15% and no more than 60% of the formulation; and
   (iii) a mixture of a $C_2$ to $C_4$ alcohol and water which mixture is present in an amount of between about 40% and 98% of the solvent system, wherein the $C_2$ to $C_4$ alcohol is present in an amount of about 5% to 80% of the mixture, and the water is present in an amount of about 20% to 95% of the mixture, so that, compared to formulations containing the same (i) and (ii) components but in different amounts and ratios, the present solvent system (a) inhibits crystallization of the at least one active ingredient on a skin or mucosal surface of a mammal, (b) reduces or prevents transfer of the formulation to clothing or to another being, (c) modulates biodistribution of the at least one active agent within different layers of skin, (d) facilitates absorption of the at least one active agent by a skin or a mucosal surface of a mammal, or (e) provides a combination of one or more of (a) through (d).

2. The non occlusive pharmaceutical formulation of claim 1, wherein the nicotine compound is nicotine, nicotine free base, a pharmaceutically acceptable complex of nicotine, a pharmaceutically acceptable salt of nicotine, or a mixture thereof.

3. The non occlusive pharmaceutical formulation of claim 2, wherein the pharmaceutically acceptable salt of nicotine is nicotine hydrogen tartrate or nicotine bitartrate dihydrate.

4. The non occlusive pharmaceutical formulation of claim 1, wherein the nicotine compound is presented at a concentration of about 0.5 to about 5 weight percent of nicotine free base equivalents and wherein the monoalkyl ether of diethylene glycol and the glycol are present in a weight ratio of 1:2 to 1:10.

5. The non occlusive pharmaceutical formulation of claim 1, wherein the nicotine compound is presented at a concentration of about 1 to about 2 weight percent of nicotine free base equivalents wherein the monoalkyl ether of diethylene glycol and the glycol are present in a weight ratio of 1:2 to 1:10.

6. The non occlusive pharmaceutical formulation of claim 1, wherein the monoalkyl ether of diethylene glycol is selected from the group consisting of diethylene glycol mono methyl ether, and diethylene glycol mono ethyl ether or mixtures thereof, the glycol is selected from the group consisting of propylene glycol, dipropylene glycol or mixtures thereof, and the $C_2$ to $C_4$ alcohol is elected from the group consisting of ethanol, propanol, isopropanol, 1-butanol, 2-butanol, or mixtures thereof.

7. The non occlusive pharmaceutical formulation of claim 1, wherein the glycol modulates the capacity of diethylene glycol mono ethyl ether to build a skin depot, and the gel provides a surface area of 50 to 1000 $cm^2$ when applied to skin.

8. The non occlusive pharmaceutical formulation of claim 1, further including a permeation enhancer present in an amount sufficient to increase permeability of the active agent across a dermal or mucosal surface of a mammal.

9. The non occlusive pharmaceutical formulation of claim 1, further comprising an agent selected from the group consisting of permeation enhancers, preservatives, antioxidants, buffers, humectants, sequestering agents, moisturizers, surfactants, emollients, and any combination thereof.

10. The non occlusive pharmaceutical formulation of claim 9, wherein the permeation enhancer is a fatty alcohol present between 0.1% and 2% by weight of the formulation.

11. A method of delaying or inhibiting crystallization of a nicotine compound in a transdermal or transmucosal non occlusive pharmaceutical formulation, which comprises providing the formulation according to claim 1.

12. The method of claim 11, wherein the nicotine compound is nicotine free base, a pharmaceutically acceptable complex of nicotine, a pharmaceutically acceptable salt of nicotine, and mixtures thereof.

13. The method of claim 12, wherein the pharmaceutically acceptable salt of nicotine is nicotine hydrogen tartrate or nicotine bitartrate dihydrate.

14. The method of claim 11, wherein the nicotine compound is presented at a concentration of about 0.5 to about 5 weight percent of nicotine free base equivalents and the monoalkyl ether of diethylene glycol and the glycol are present in a weight ratio of 1:2 to 1:10.

15. The method of claim 11, wherein the nicotine is presented at a concentration of about 1 to about 2 weight percent of nicotine free base equivalents and the monoalkyl ether of diethylene glycol and the glycol are present in a weight ratio of 1:2 to 1:10.

16. The method of claim 11, wherein the monoalkyl ether of diethylene glycol is selected from the group consisting of diethylene glycol mono methyl ether, and diethylene glycol mono ethyl ether or mixtures thereof, the glycol is selected from the group consisting of propylene glycol, dipropylene glycol or mixtures thereof, and the $C_2$ to $C_4$ alcohol is elected from the group consisting of ethanol, propanol, isopropanol, 1-butanol, 2-butanol, or mixtures thereof.

17. The method of claim 11, wherein the glycol modulates the capacity of diethylene glycol mono ethyl ether to build a skin depot and the pH of the formulation is between about pH 4.5 and about pH 8.5.

18. The method of claim 11, further including a permeation enhancer present in an amount sufficient to increase permeability of the active agent across a dermal or mucosal surface of a mammal.

19. The method of claim 11, wherein the permeation enhancer is a fatty alcohol present in an amount of between 0.1% and 2% by weight of the formulation.

20. The method of claim 11, further comprising an agent selected from the group consisting of gelling agents; permeation enhancers, preservatives, antioxidants, buffers, humectants, sequestering agents, moisturizers, surfactants, emollients, and any combination thereof.

21. The pharmaceutical composition of claim 1 provided in a unit dose container.

22. The pharmaceutical composition of claim 21, wherein the container is a packet or a vial, wherein the inner surface of the container optionally comprises a liner.

23. The pharmaceutical composition of claim 22, wherein the packet is a flexible, foil packet and the liner is a polyethylene liner.

24. The pharmaceutical composition of claim 1 provided in a multiple dose container.

25. The pharmaceutical composition of claim 24, wherein the multiple dose container dispenses fixed or variable metered doses and optionally includes a stored-energy metered dose pump or a manual metered dose pump.

26. A method for administering an active agent to a human subject in need thereof, the method comprising:
providing a gel for pharmaceutical drug delivery, comprising:
a therapeutically effective amount of a nicotine compound, or a pharmaceutically acceptable salt thereof;
a solvent system present in an amount sufficient to solubilize the nicotine and characterized in that it includes:
(i) a pharmaceutically acceptable monoalkyl ether of diethylene glycol present in an amount of between about 1% and 30% by weight of the solvent system;
(ii) a pharmaceutically acceptable glycol present in an amount of between about 1% and 30% by weight of the solvent system, with the monoalkyl ether of diethylene glycol and glycol being present in a weight ratio of 10:1 to 2:1 or 1:2 to 1:10; and
(iii) a mixture of a $C_2$ to $C_4$ alcohol and water which mixture is present in an amount of between about 40% and 98% of the solvent system, wherein the C2 to C4 alcohol is present in an amount of about 5% to 80% of the mixture, and the water is present in an amount of about 20% to 95% of the mixture,
applying one or more daily dose of the gel to a skin surface of the subject in an amount sufficient for the nicotine to achieve therapeutic concentration in the bloodstream of the subject.

27. The method of claim 26, wherein the human subject is in need of nicotine therapy to treat smoking cessation.

28. The method of claim 26, wherein the human subject is in need of nicotine therapy to treat irritable bowel syndrome.

29. The method of claim 26, wherein the human subject is in need of nicotine therapy to treat neurological disorders, selected from the group consisting of anxiety, depression, schizophrenia, Alzheimer's Disease, Parkinson's Disease, Restless Legs Syndrome, Tourette's Syndrome, Chronic Tic Disorder, Essential Tremor, and Attention Deficit Hyperactivity Disorder.

30. The method of claim 26, wherein the gel has an amount of nicotine free base equivalents between about 0.5 and about 5 weight percent and up to about 10 grams of the gel is applied daily to a skin surface area of between about 50 to about 1000 $cm^2$ in single or divided doses.

31. The pharmaceutical composition of claim 1 provided in a dosage form for delivery of nicotine to a subject,
wherein said dosage form is configured to provide steady-state delivery of nicotine with once-a-day dosing.

32. The pharmaceutical composition of claim 31, wherein said once-a-day dosing is performed for at least about 2 successive days.

33. The pharmaceutical composition of claim 31, wherein said dosage form comprises a dose of nicotine between about 0.5 to about 5 weight percent of nicotine free base equivalents.

* * * * *

UNITED STATES PATENT AND TRADEMARK OFFICE
CERTIFICATE OF CORRECTION

| | | |
|---|---|---|
| PATENT NO. | : 7,387,788 B1 | Page 1 of 1 |
| APPLICATION NO. | : 11/492568 | |
| DATED | : June 17, 2008 | |
| INVENTOR(S) | : Carrara et al. | |

It is certified that error appears in the above-identified patent and that said Letters Patent is hereby corrected as shown below:

Drawings:
Sheet 2 of 9 of the drawings, correct the identification of "Fig. 2Abis" to -- Fig. 1Bbis--

Signed and Sealed this

Ninth Day of September, 2008

JON W. DUDAS
*Director of the United States Patent and Trademark Office*